(12) United States Patent
Moore et al.

(10) Patent No.: US 12,400,744 B2
(45) Date of Patent: Aug. 26, 2025

(54) FREEFORM TEXT ANALYSIS AND PROCESSING FOR NEUROSTIMULATION DATA

(71) Applicant: Boston Scientific Neuromodulation Corporation, Valencia, CA (US)

(72) Inventors: Lisa Denise Moore, Glendale, CA (US); Bradley Lawrence Hershey, Carrollton, TX (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 135 days.

(21) Appl. No.: 18/228,938

(22) Filed: Aug. 1, 2023

(65) Prior Publication Data

US 2024/0055085 A1   Feb. 15, 2024

Related U.S. Application Data

(60) Provisional application No. 63/396,533, filed on Aug. 9, 2022.

(51) Int. Cl.
   *G06F 40/279*    (2020.01)
   *G06F 40/166*    (2020.01)
   (Continued)

(52) U.S. Cl.
   CPC ........... *G16H 10/60* (2018.01); *G06F 40/166* (2020.01); *G06F 40/279* (2020.01); *G16H 20/30* (2018.01); *G16H 50/50* (2018.01); *G16H 50/70* (2018.01)

(58) Field of Classification Search
   IPC ...................... G06Q 10/06,30/00, 30/02, 10/00, 10/0637, 50/00; G16H 10/60, 20/30, 15/00, 20/70, 40/20, 40/60, 40/67, 50/20, 50/30, 50/50, 10/20, 20/00, 30/40, 40/63, 50/70, 80/00
   See application file for complete search history.

(56) References Cited

U.S. PATENT DOCUMENTS 8,441,356 B1 *  5/2013  Tedesco ............. G08B 21/0453
                                              340/539.15
9,767,255 B2 *  9/2017  Kaula ..................... G16H 40/63
(Continued)

*Primary Examiner* — Rayeez R Chowdhury
(74) *Attorney, Agent, or Firm* — Schwegman Lundberg & Woessner, P.A.

(57) ABSTRACT

Systems and techniques are disclosed to process freeform data relating to neurostimulation treatment of a human patient, to determine relevant attributes and information regarding a state of the patient. In an example, a system to process freeform data implements electronic operations to: obtain freeform input that indicates characteristics of a neurostimulation treatment of a human patient; validate the freeform input; identify attributes associated with a state of the human patient, based on words from the validated freeform input; associate the attributes with the validated freeform input; and store data for the validated freeform input and the associated attributes. Specific operations for validating may include excluding or replacing words, and specific operations for identifying attributes may be based on natural language processing. Such processing of the freeform data may be used to identify results of neurostimulation programs, and effect improvements to neurostimulation programming or usage.

20 Claims, 10 Drawing Sheets

(51) Int. Cl.
*G16H 10/60* (2018.01)
*G16H 20/30* (2018.01)
*G16H 50/50* (2018.01)
*G16H 50/70* (2018.01)

(56) References Cited

U.S. PATENT DOCUMENTS

| | | | |
|---|---|---|---|
| 2012/0330355 A1* | 12/2012 | Finley | A61B 17/0401 606/232 |
| 2014/0067411 A1* | 3/2014 | Kaula | G16H 40/63 705/2 |
| 2019/0172586 A1* | 6/2019 | Choksi | G16H 10/60 |
| 2019/0206563 A1* | 7/2019 | Shelton, IV | A61B 34/20 |
| 2023/0247169 A1* | 8/2023 | Garcia i Tormo | A61B 5/165 348/14.03 |

* cited by examiner

FREEFORM TEXT ANALYSIS AND PROCESSING FOR NEUROSTIMULATION DATA

CLAIM OF PRIORITY

This application claims the benefit of U.S. Provisional Application No. 63/396,533, filed on Aug. 9, 2022, which is hereby incorporated by reference in its entirety.

TECHNICAL FIELD

The present disclosure relates generally to data processing obtained in connection with the use of medical devices, and more particularly, to systems, devices, and methods for processing data and metadata obtained from clinician(s) or patient(s) in connection with implanted electrical stimulation, including freeform textual data obtained in connection with neurostimulation treatments used for pain treatment, movement disorders, and/or management of such conditions.

BACKGROUND

Neurostimulation, also referred to as neuromodulation, has been proposed as a therapy for a number of conditions. Examples of neurostimulation include Spinal Cord Stimulation (SCS), Deep Brain Stimulation (DBS), Peripheral Nerve Stimulation (PNS), and Functional Electrical Stimulation (FES). Implantable neurostimulation systems have been applied to deliver such a therapy. An implantable neurostimulation system may include an implantable neurostimulator, also referred to as an implantable pulse generator (IPG), and one or more implantable leads each including one or more electrodes. The implantable neurostimulator delivers neurostimulation energy through one or more electrodes placed on or near a target site in the nervous system.

A neurostimulation system can be used to electrically stimulate tissue or nerve centers to treat nervous or muscular disorders. For example, an SCS system may be configured to deliver electrical pulses to a specified region of a patient's spinal cord, such as particular spinal nerve roots or nerve bundles, to produce an analgesic effect that masks pain sensation, or to produce a functional effect that allows increased movement or activity of the patient. Other forms of neurostimulation may include a DBS system which uses similar pulses of electricity at particular locations in the brain to reduce symptoms of essential tremors, Parkinson's disease, psychological disorders, or the like.

In connection with a treatment of a particular patient using a neurostimulation system, a variety of data is monitored and collected, including data obtained from a clinician and overseeing medical professionals and data obtained directly from the patient. For example, data that is collected from the patient may include questionnaire answers or open-ended feedback that provides details on the patient's health, the efficacy of the neurostimulation treatment, objective or subjective information about the effectiveness of the neurostimulation treatment, side effects or problems from the neurostimulation treatment, and the like. Although this collected data provides a valuable source of information, it is often collected as unstructured data (e.g., freeform narrative text) and includes personal or privacy-protected health information. As a result, such collected data is often not used or analyzed as part of the neurostimulation treatment workflow.

SUMMARY

The following Summary provides examples as an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

Example 1 is a system to process freeform data relating to neurostimulation treatment, the system comprising: at least one processor; and at least one memory device comprising instructions, which when executed by the processor, cause the processor to perform operations that: obtain freeform input, the freeform input indicating one or more characteristics of a neurostimulation treatment of a human patient; validate the freeform input; identify one or more attributes associated with a state of the human patient, based on one or more words from the validated freeform input; associate the one or more attributes with the validated freeform input; and store data for the validated freeform input and the one or more associated attributes.

In Example 2, the subject matter of Example 1 optionally includes subject matter where the operations to validate the freeform input include operations that: identify one or more words for exclusion in the freeform input, based on an exclusion word list; and remove the one or more words for exclusion from the freeform input, to produce the validated freeform input.

In Example 3, the subject matter of Example 2 optionally includes subject matter where the exclusion word list is determined based on natural language processing of the freeform input.

In Example 4, the subject matter of any one or more of Examples 1-3 optionally include subject matter where the operations to validate the freeform input include operations that: identify one or more words for inclusion in the freeform input, based on an allowed word list; and select the one or more words from the freeform input, to produce the validated freeform input.

In Example 5, the subject matter of Example 4 optionally includes subject matter where the allowed word list is based on natural language processing of the freeform input.

In Example 6, the subject matter of any one or more of Examples 1-5 optionally include subject matter where the operations to validate the freeform input include operations that: anonymize the freeform input, to remove personally identifying information from the freeform input.

In Example 7, the subject matter of Example 6 optionally includes subject matter where the operations to validate the freeform input further include operations that: obtain user validation of the anonymized freeform input.

In Example 8, the subject matter of any one or more of Examples 1-7 optionally include subject matter where the one or more attributes indicate a state of a medical condition or a state of the neurostimulation treatment for the human patient, wherein the one or more attributes are identified using natural language processing of the one or more words from the validated freeform input, and wherein the instructions further perform operations that: identify the state of the medical condition from one or more of: medication data, sensor data, or neurostimulation device data; and identify the state of the neurostimulation treatment from one or more of: prior neurostimulation settings, current neurostimulation settings, or scheduled programmed neurostimulation settings.

In Example 9, the subject matter of any one or more of Examples 1-8 optionally include subject matter where the state of the human patient relates to at least one physiological condition identified from the validated freeform input, and wherein the at least one physiological condition is associated with: pain measurements, pain states, sleep measurements, sleep states, movement, activity, mobility, physical function, cardiac function, autonomic function, medication, or emotional state, of the human patient.

In Example 10, the subject matter of any one or more of Examples 1-9 optionally include subject matter where the freeform input originates from the human patient, a caregiver, or a medical professional associated with the human patient.

In Example 11, the subject matter of any one or more of Examples 1-10 optionally include subject matter where operations to associate the one or more attributes with the validated freeform input include operations that: match use of at least one neurostimulation program to the state of the human patient, based on usage of the at least one neurostimulation program in a neurostimulation device implanted in the human patient.

In Example 12, the subject matter of any one or more of Examples 1-11 optionally include subject matter where the freeform input originates from a text input or an audio input converted to text.

In Example 13, the subject matter of any one or more of Examples 1-12 optionally include subject matter where the operations to store the data cause the data to be stored in a remote database maintaining data for a plurality of human patients.

Example 14 is a machine-readable medium including instructions, which when executed by a machine, cause the machine to perform the operations of the system of any of the Examples 1 to 13.

Example 15 is a method to perform the operations of the system of any of the Examples 1 to 13.

Example 16 is a device to process freeform data relating to neurostimulation treatment, the device comprising: at least one processor and at least one memory; input data processing circuitry, operable with the processor and the memory, the data processing circuitry configured to: receive freeform input, the freeform input indicating one or more characteristics of a neurostimulation treatment of a human patient; and identify text from the freeform input; text processing circuitry, operable with the processor and the memory, the text processing circuitry configured to: validate the freeform input; identify one or more attributes associated with a state of the human patient, based on one or more words from the validated freeform input; and patient state data processing circuitry, in operation with the at least one processor and the at least one memory, configured to: associate the one or more attributes with the validated freeform input; and output data for the validated freeform input and the one or more associated attributes.

In Example 17, the subject matter of Example 16 optionally includes subject matter where to validate the freeform input includes to: identify one or more words for exclusion in the freeform input, based on an exclusion word list; and remove the one or more words for exclusion from the freeform input, to produce the validated freeform input; wherein the exclusion word list is determined based on natural language processing of the freeform input.

In Example 18, the subject matter of any one or more of Examples 16-17 optionally include subject matter where to validate the freeform input includes to: identify one or more words for inclusion in the freeform input, based on an allowed word list; and select the one or more words from the freeform input, to produce the validated freeform input; wherein the allowed word list is based on natural language processing of the freeform input.

In Example 19, the subject matter of any one or more of Examples 16-18 optionally include subject matter where to validate the freeform input includes to: anonymize the freeform input, to remove personally identifying information from the freeform input.

In Example 20, the subject matter of Example 19 optionally includes subject matter where to validate the freeform input further includes to obtain user validation of the anonymized freeform input.

In Example 21, the subject matter of any one or more of Examples 16-20 optionally include subject matter where the one or more attributes indicate a state of a medical condition or a state of the neurostimulation treatment for the human patient, wherein the one or more attributes are identified using natural language processing of the one or more words from the validated freeform input, and wherein identifying the one or more attributes further includes: identify the state of the medical condition from one or more of: medication data, sensor data, or neurostimulation device data; and identify the state of the neurostimulation treatment from one or more of: prior neurostimulation settings, current neurostimulation settings, or scheduled programmed neurostimulation settings.

In Example 22, the subject matter of any one or more of Examples 16-21 optionally include subject matter where the state of the human patient relates to at least one physiological condition identified from the validated freeform input, and wherein the at least one physiological condition is associated with: pain measurements, pain states, sleep measurements, sleep states, movement, activity, mobility, physical function, cardiac function, autonomic function, medication, or emotional state, of the human patient.

In Example 23, the subject matter of any one or more of Examples 16-22 optionally include subject matter where to associate the one or more attributes with the validated freeform input includes to: match use of at least one neurostimulation program to the state of the human patient, based on usage of the at least one neurostimulation program in a neurostimulation device implanted in the human patient.

In Example 24, the subject matter of any one or more of Examples 16-23 optionally include subject matter where the freeform input originates from the human patient, a caregiver, or a medical professional associated with the human patient, and wherein the freeform input originates from a text input or an audio input converted to text.

In Example 25, the subject matter of any one or more of Examples 16-24 optionally include subject matter where to store the data includes causing the data to be stored in a remote database maintaining data for a plurality of human patients.

Example 26 is a method for processing freeform data relating to neurostimulation treatment, comprising: receiving freeform input, the freeform input indicating one or more characteristics of a neurostimulation treatment of a human patient; validating the freeform input; identifying one or more attributes associated with a state of the human patient, based on one or more words from the validated freeform input; associating the one or more attributes with the validated freeform input; and storing data for the validated freeform input and the one or more associated attributes.

In Example 27, the subject matter of Example 26 optionally includes subject matter where validating the freeform input comprises: identifying one or more words for exclusion in the freeform input, based on an exclusion word list; and removing the one or more words for exclusion from the freeform input, to produce the validated freeform input; wherein the exclusion word list is determined based on natural language processing of the freeform input.

In Example 28, the subject matter of any one or more of Examples 26-27 optionally include subject matter where validating the freeform input comprises: identifying one or more words for inclusion in the freeform input, based on an allowed word list; and selecting the one or more words from the freeform input, to produce the validated freeform input; wherein the allowed word list is based on natural language processing of the freeform input.

In Example 29, the subject matter of any one or more of Examples 26-28 optionally include subject matter where validating the freeform input comprises: anonymizing the freeform input, to remove personally identifying information from the freeform input.

In Example 30, the subject matter of Example 29 optionally includes subject matter where validating the freeform input comprises: obtaining user validation of the anonymized freeform input.

In Example 31, the subject matter of any one or more of Examples 26-30 optionally include subject matter where the one or more attributes indicate a state of a medical condition or a state of the neurostimulation treatment for the human patient, wherein the one or more attributes are identified using natural language processing of the one or more words from the validated freeform input, and wherein identifying the one or more attributes further comprises: identifying the state of the medical condition from one or more of: medication data, sensor data, or neurostimulation device data; and identifying the state of the neurostimulation treatment from one or more of: prior neurostimulation settings, current neurostimulation settings, or scheduled programmed neurostimulation settings.

In Example 32, the subject matter of any one or more of Examples 26-31 optionally include subject matter where the state of the human patient relates to at least one physiological condition identified from the validated freeform input, and wherein the at least one physiological condition is associated with: pain measurements, pain states, sleep measurements, sleep states, movement, activity, mobility, physical function, cardiac function, autonomic function, medication, or emotional state, of the human patient.

In Example 33, the subject matter of any one or more of Examples 26-32 optionally include subject matter where associating the one or more attributes with the validated freeform input comprises: matching use of at least one neurostimulation program to the state of the human patient, based on usage of the at least one neurostimulation program in a neurostimulation device implanted in the human patient.

In Example 34, the subject matter of any one or more of Examples 26-33 optionally include subject matter where the freeform input originates from the human patient, caregiver, or a medical professional associated with the human patient, and wherein the freeform input originates from a text input or an audio input converted to text.

In Example 35, the subject matter of any one or more of Examples 26-34 optionally include subject matter where to store the data comprises causing the data to be stored in a remote database maintaining data for a plurality of human patients.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
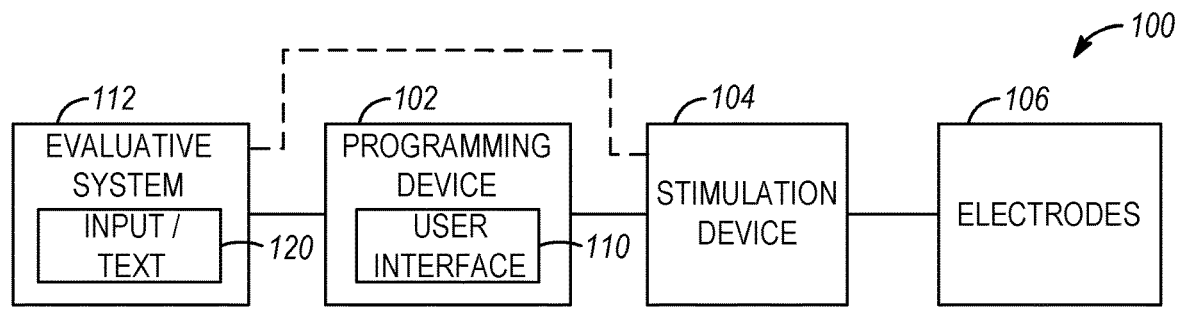
FIG. 1 illustrates, by way of example, an embodiment of a neurostimulation system.

This document discusses various techniques for the collection, processing, storage, and communication of data relevant to treatment with an implantable electrical neurostimulation device. Such data includes unstructured data provided from freeform text or audio input, which is relevant to the neurostimulation treatment of pain, movement disorders, or related physiological conditions in a human subject (e.g., a patient). As an example, various systems and methods are described to identify, redact, anonymize, store, and propagate patient state data, based on the evaluation of patient freeform text and similar forms of unstructured or unclassified data.

In some existing approaches of neurostimulation treatment, a patient provides detailed feedback to a clinician in limited settings, such as during a scheduled doctor's visit where the patient indicates the effectiveness of the neurostimulation. In other settings, such as during clinical trials, a patient may be provided with open-ended questions with a regular questionnaire in order to ask if any issues are occurring with the neurostimulation device or the device programming. The present techniques and systems improve this and related scenarios through the collection and analysis of unstructured data using textual analysis and other analytical methods.

In various examples, freeform input is obtained from a patient or clinician as text (or converted into text), and processed with the text redaction or anonymization techniques discussed below. The text is then analyzed with natural language processing to determine relevant patient state information, based on relevance to a particular neurostimulation treatment. The information derived from the patient freeform input may be used in a variety of subsequent systems and downstream use cases. For example, derived information may be used to identify issues with the operation of a particular device, device operation mode, medical condition, or changes to neurostimulation or other medical treatments. The derived information also may be used to produce logging, reports, and alerts for clinicians or other entities who oversee treatment or device operation. Likewise, such derived information may even be used for open-loop and closed-loop programming modifications, such as to suggest or automatically implement changes to device programming when a particular condition is identified.

The following discussion provide an introduction to the features of an example neurostimulation system and how a neurostimulation system is programmed to cause specific effects on a subject patient. These effects, as well as other patient state data, then may be identified from later-provided freeform inputs from the patient or clinician. While neurostimulation therapies, such as SCS and DBS therapies, are specifically discussed as examples, the present subject matter may apply to other therapies that employ stimulation pulses of electrical or other forms of energy for treating chronic pain or similar physiological or medical conditions.

FIG. 1 illustrates an embodiment of a neurostimulation system 100. System 100 includes electrodes 106, a stimulation device 104, and a programming device 102. Electrodes 106 are configured to be placed on or near one or more neural targets in a patient. Stimulation device 104 is configured to be electrically connected to electrodes 106 and deliver neurostimulation energy, such as in the form of electrical pulses, to the one or more neural targets though electrodes 106. The delivery of the neurostimulation is controlled by using a plurality of stimulation parameters, such as stimulation parameters specifying a pattern of the electrical pulses and a selection of electrodes through which each of the electrical pulses is delivered. In various embodiments, at least some parameters of the plurality of stimulation parameters are selected or programmable by a clinical user, such as a physician or other caregiver who treats the patient using system 100; however, some of the parameters may also be provided in connection with closed-loop programming logic and adjustment. Programming device 102 provides the user with accessibility to implement, change, or modify the programmable parameters. In various embodiments, programming device 102 is configured to be communicatively coupled to stimulation device 104 via a wired or wireless link.

In various embodiments, programming device 102 includes a user interface 110 (e.g., a user interface embodied by a graphical, text, voice, or hardware-based user interface) that allows the user to set and/or adjust values of the user-programmable parameters by creating, editing, loading, and removing programs that include parameter combinations such as patterns and waveforms. Such waveforms may include, for example, the waveform of a pattern of neurostimulation pulses to be delivered to the patient as well as individual waveforms that are used as building blocks of the pattern of neurostimulation pulses. Examples of such individual waveforms include pulses, pulse groups, and groups of pulse groups. The program and respective sets of parameters may also define an electrode selection specific to each individually defined waveform.

The delivery of neurostimulation energy that is discussed herein may be delivered in the form of electrical neurostimulation pulses. The delivery is controlled using stimulation parameters that specify spatial (where to stimulate), temporal (when to stimulate), and informational (patterns of pulses directing the nervous system to respond as desired) aspects of a pattern of neurostimulation pulses. Many current neurostimulation systems are programmed to deliver periodic pulses with one or a few uniform waveforms continuously or in bursts. However, neural signals may include more sophisticated patterns to communicate various types of information, including sensations of pain, pressure, temperature, etc.

The present approaches further provide examples of an evaluative system 112, such as a patient data analysis system, that is used to analyze freeform inputs (e.g., input text 120) related to a neurostimulation treatment occurring from stimulation device 104. This evaluative system 112 can initiate a data processing action related to patient data or state of the neurostimulation treatment based on analysis performed on input text 120. The input text 120 may be collected from the patient or clinician, such as with text entered via user interface 110 and then analyzed by the evaluative system 112. The evaluative system 112 may reside at a remote computing system, such as a cloud server that provides services to perform freeform input processing on demand when invoked by the user interface 110 or other entities. In various examples, in addition to collecting information from the freeform input, the evaluative system 112 may also directly or indirectly collect information regarding the patient or the neurostimulation treatment by being communicatively coupled with programming device 102 or stimulation device 104.

As described in more detail below with respect to the data flows in FIGS. 7 to 12, a user can provide freeform inputs to the evaluative system 112, to collect information on the neurostimulation treatment that is implemented by the stimulation device 104 or the operation of the stimulation device 104. The evaluative system 112 may perform one or more actions to identify, extract, filter, redact, or classify concepts in the freeform inputs, such as through the use of natural language processing other algorithmic processing.

Example parameters that can be implemented by a selected neurostimulation program include, but are not limited to the following: amplitude, pulse width, frequency, duration, total charge injected per unit time, cycling (e.g., on/off time), pulse shape, number of phases, phase order, interphase time, charge balance, ramping, as well as spatial variance (e.g., electrode configuration changes over time). As detailed in FIG. 6, a controller, e.g., controller 630 of FIG. 6, can implement program(s) and parameter setting(s) to affect a specific neurostimulation waveform, pattern, or energy output, using a program or setting in storage, e.g., external storage device 616 of FIG. 6, or using settings communicated via an external communication device 618 of FIG. 6 corresponding to the selected program. The implementation of such program(s) or setting(s) may further define a therapy strength and treatment type corresponding to a specific pulse group, or a specific group of pulse groups, based on the specific programs or settings. The evaluative system 112 and the evaluation of the input text 120 provides a mechanism to determine the effectiveness of such programs or settings for a particular patient, and to classify particular treatment states and associated medical outcomes in an indirect or direct manner.

Portions of the evaluative system 112, the stimulation device 104 (e.g., implantable medical device), or the programming device 102 can be implemented using hardware, software, or any combination of hardware and software. Portions of the stimulation device 104 or the programming device 102 may be implemented using an application-specific circuit that can be constructed or configured to perform one or more particular functions, or can be implemented using a general-purpose circuit that can be programmed or otherwise configured to perform one or more particular functions. Such a general-purpose circuit can include a microprocessor or a portion thereof, a microcontroller or a portion thereof, or a programmable logic circuit, or a portion thereof. The system 100 could also include a subcutaneous medical device (e.g., subcutaneous ICD, subcutaneous diagnostic device), wearable medical devices (e.g., patch-based sensing device), or other external medical devices.

Figure 2:
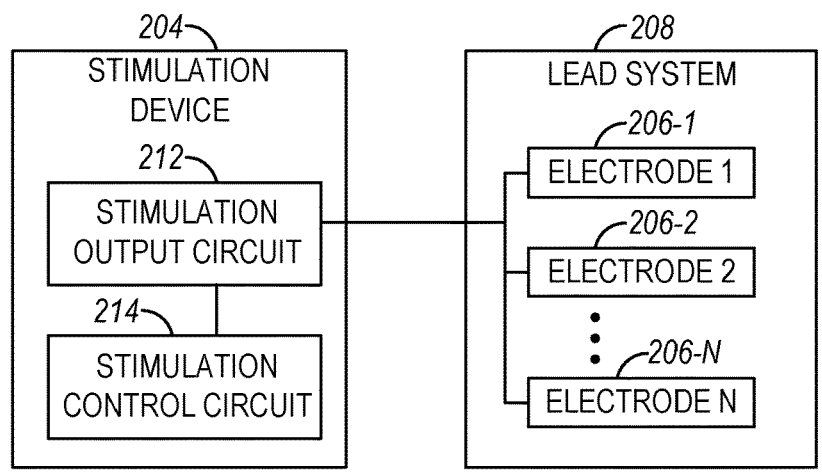
FIG. 2 illustrates, by way of example, an embodiment of a stimulation device and a lead system, such as may be implemented in the neurostimulation system of FIG. 1.

FIG. 2 illustrates an embodiment of a stimulation device 204 and a lead system 208, such as may be implemented in neurostimulation system 100 of FIG. 1. Stimulation device 204 represents an embodiment of stimulation device 104 and includes a stimulation output circuit 212 and a stimulation control circuit 214. Stimulation output circuit 212 produces and delivers neurostimulation pulses, including the neurostimulation waveform and parameter settings implemented via a program selected or implemented with the user interface 110. Stimulation control circuit 214 controls the delivery of the neurostimulation pulses using the plurality of stimulation parameters, which specifies a pattern of the neurostimulation pulses. Lead system 208 includes one or more leads each configured to be electrically connected to stimulation device 204 and a plurality of electrodes 206 distributed in the one or more leads. The plurality of electrodes 206 includes electrode 206-1, electrode 206-2, ... electrode 206-N, each a single electrically conductive contact providing for an electrical interface between stimulation output circuit 212 and tissue of the patient, where N≥2. The neurostimulation pulses are each delivered from stimulation output circuit 212 through a set of electrodes selected from electrodes 206. In various embodiments, the neurostimulation pulses may include one or more individually defined pulses, and the set of electrodes may be individually definable by the user for each of the individually defined pulses.

In various embodiments, the number of leads and the number of electrodes on each lead depend on, for example, the distribution of target(s) of the neurostimulation and the need for controlling the distribution of electric field at each target. In one embodiment, lead system 208 includes 2 leads each having 8 electrodes. Those of ordinary skill in the art will understand that the neurostimulation system 100 may include additional components such as sensing circuitry for patient monitoring and/or feedback control of the therapy, telemetry circuitry, and power. The neurostimulation system 100 may also integrate with other sensors, or such other sensors may independently provide information for use with programming of the neurostimulation system 100, and for data collection and evaluation (e.g., to be associated with freeform input).

The neurostimulation system 100 may be configured to modulate spinal target tissue or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "modulation parameter" set. Each set of modulation parameters, including fractionalized current distribution to the electrodes (as percentage cathodic current, percentage anodic current, or off), may be stored and combined into a program that can then be used to modulate multiple regions within the patient.

The neurostimulation system 100 may be configured to deliver different electrical fields to achieve a temporal summation of modulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields can be rotated or cycled through multiple times under a timing scheme, where each field is implemented using a timing channel. The electrical fields may be generated at a continuous pulse rate, or as bursts of pulses. Furthermore, the interpulse interval (i.e., the time between adjacent pulses), pulse amplitude, and pulse duration during the electrical field cycles may be uniform or may vary within the electrical field cycle. In some examples, the modulation field may be shaped to enhance modulation of some neural structures and diminish modulation at other neural structures. The modulation field may be shaped by using multiple independent current control (MICC) or multiple independent voltage control to guide the estimate of current fractionalization among multiple electrodes and estimate a total amplitude that provide a desired strength. For example, the modulation field may be shaped to enhance the modulation of dorsal horn neural tissue and to minimize the modulation of dorsal column tissue.

Figure 3:
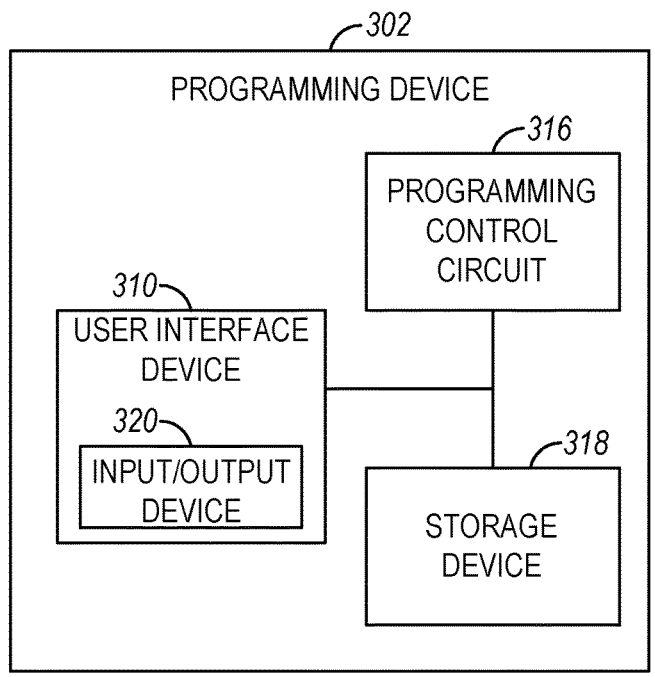
FIG. 3 illustrates, by way of example, an embodiment of a programming device, such as may be implemented in the neurostimulation system of FIG. 1.

FIG. 3 illustrates an embodiment of a programming device 302, such as may be implemented in neurostimulation system 100. Programming device 302 represents an embodiment of programming device 102 and includes a storage device 318, a programming control circuit 316, and a user interface device 310. Programming control circuit 316 generates the plurality of stimulation parameters that controls the delivery of the neurostimulation pulses according to the pattern of the neurostimulation pulses. The user interface device 310 represents an embodiment to implement the user interface 110.

In various embodiments, the user interface device 310 includes an input/output device 320 that is capable to receive user interaction and commands to load, modify, and implement neurostimulation programs and schedule delivery of the neurostimulation programs. In various embodiments, the input/output device 320 allows the user to create, establish, access, and implement respective parameter values of a neurostimulation program through graphical selection (e.g., in a graphical user interface output with the input/output device 320), or other graphical input/output relating to therapy objectives, efficacy of applied treatment, user feedback, and the like. In various examples, the user interface device 310 can receive user input to initiate or control the implementation of the programs or program changes which are recommended, modified, selected, or loaded through use of an open or closed loop programming system.

In various embodiments, the input/output device 320 allows the patient user to apply, change, modify, or discontinue certain building blocks of a program and a frequency at which a selected program is delivered. In various embodiments, the input/output device 320 can allow the patient user to save, retrieve, and modify programs (and program settings), such as from programs that are loaded from a clinical encounter or pre-programmed (e.g., as templates). In various embodiments, the input/output device 320 and accompanying software on the user interface device 310 allows newly created building blocks, program components, programs, and program modifications to be saved, stored, or otherwise persisted in storage device 318. Thus, it will be understood that the user interface device 310 may allow many forms of device operation and control, even if closed loop programming is occurring.

The user interface device 310 may provide an interactive mechanism, controllable with the input/output device 320, for the input of freeform text or audio. In one embodiment, the input/output device 320 includes a touchscreen. In various embodiments, the input/output device 320 includes any type of presentation device, such as interactive or non-interactive screens, and any type of user input device that allows the user to interact with a user interface to implement, remove, or schedule the programs. Thus, the input/output device 320 may include one or more of a touchscreen, keyboard, keypad, touchpad, trackball, joystick, and mouse. The logic of the user interface 110, the stimulation control circuit 214, and the programming control circuit 316, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 4:
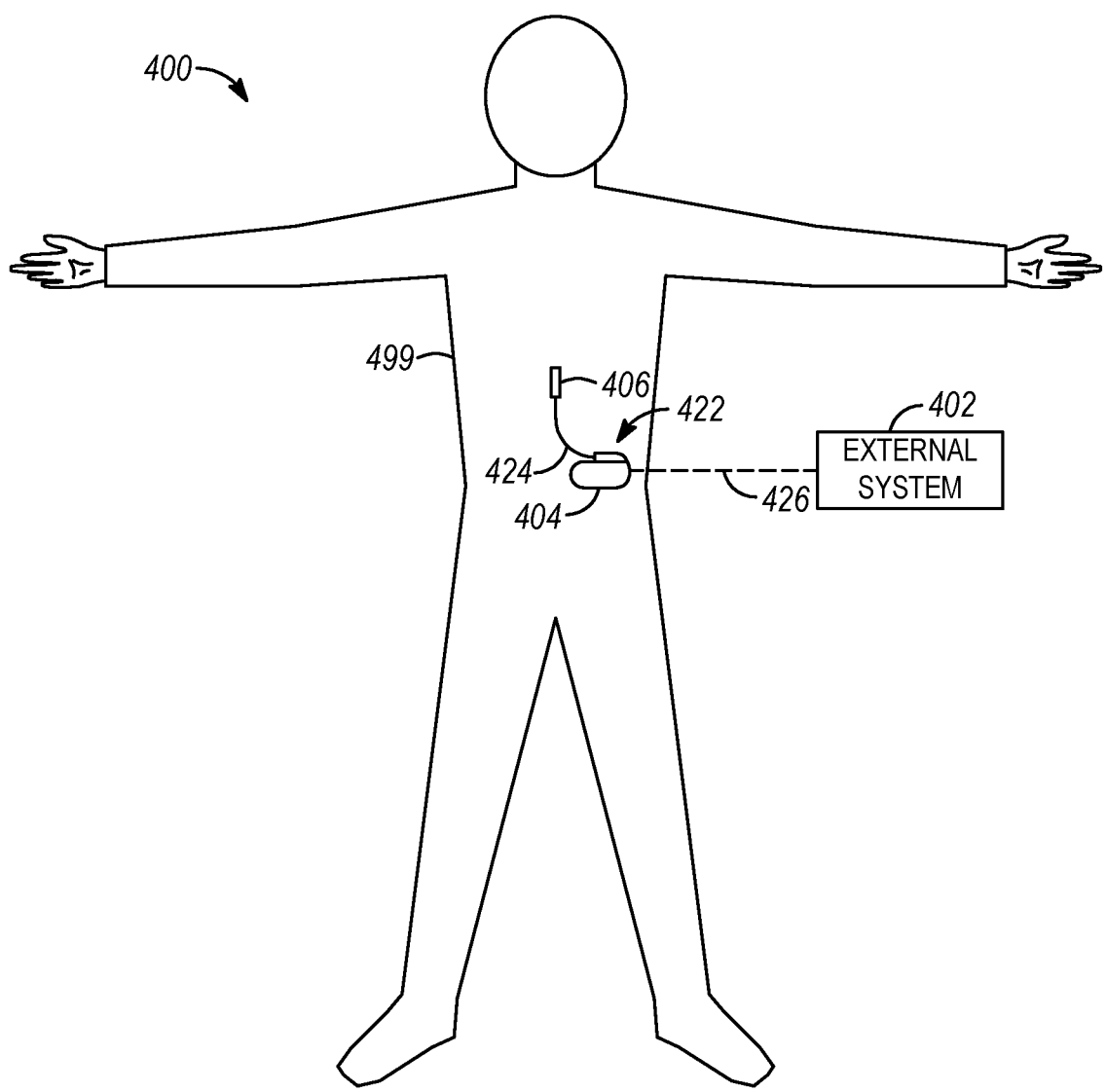
FIG. 4 illustrates, by way of example, an implantable neurostimulation system and portions of an environment in which the system may be used.

FIG. 4 illustrates an implantable neurostimulation system 400 and portions of an environment in which system 400 may be used. System 400 includes an implantable system 422, an external system 402, and a telemetry link 426 providing for wireless communication between an implantable system 422 and an external system 402. Implantable system 422 is illustrated in FIG. 4 as being implanted in the patient's body 499. The system is illustrated for implantation near the spinal cord. However, the neuromodulation system may be configured to modulate other neural targets.

Implantable system 422 includes an implantable stimulator 404 (also referred to as an implantable pulse generator, or IPG), a lead system 424, and electrodes 406, which represent an embodiment of the stimulation device 204, the lead system 208, and the electrodes 206, respectively. The external system 402 represents an embodiment of the programming device 302.

In various embodiments, the external system 402 includes one or more external (non-implantable) devices each allowing the user and/or the patient to communicate with the implantable system 422. In some embodiments, the external system 402 includes a programming device intended for the user to initialize and adjust settings for the implantable stimulator 404 and a remote control device intended for use by the patient. For example, the remote control device may allow the patient to turn the implantable stimulator 404 on and off and/or adjust certain patient-programmable parameters of the plurality of stimulation parameters. The remote control device may also provide a mechanism to receive and process feedback on the operation of the implantable neuromodulation system. Feedback may include metrics or an efficacy indication reflecting perceived pain, effectiveness of therapies, or other aspects of patient comfort or condition. Such feedback may be automatically detected from a patient's physiological state, collected from other sensors or devices (not shown), or manually obtained from user input entered in a user interface (such as with the user input scenarios discussed below).

As used herein, the terms "neurostimulator," "stimulator," "neurostimulation," and "stimulation" generally refer to the delivery of electrical energy that affects the neuronal activity of neural tissue, which may be excitatory or inhibitory; for example by initiating an action potential, inhibiting or blocking the propagation of action potentials, affecting changes in neurotransmitter/neuromodulator release or uptake, and inducing changes in neuro-plasticity or neurogenesis of tissue. It will be understood that other clinical effects and physiological mechanisms may also be provided through use of such stimulation techniques.

Figure 5:
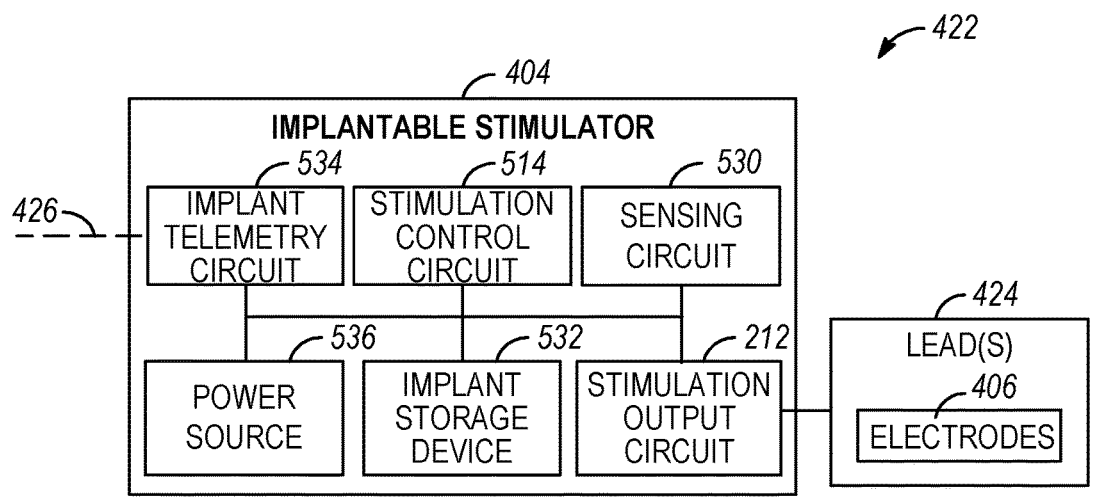
FIG. 5 illustrates, by way of example, an embodiment of an implantable stimulator and one or more leads of a neurostimulation system, such as the implantable neurostimulation system of FIG. 4.

FIG. 5 illustrates an embodiment of the implantable stimulator 404 and the one or more leads 424 of an implantable neurostimulation system, such as the implantable system 422. The implantable stimulator 404 may include a sensing circuit 530 used for an optional sensing capability, stimulation output circuit 212, a stimulation control circuit 514, an implant storage device 532, an implant telemetry circuit 534, and a power source 536. The sensing circuit 530, when included and needed, senses one or more physiological signals for purposes of patient monitoring and/or feedback control of the neurostimulation. Examples of the one or more physiological signals includes neural and other signals each indicative of a condition of the patient that is treated by the neurostimulation and/or a response of the patient to the delivery of the neurostimulation.

The stimulation output circuit 212 is electrically connected to electrodes 406 through the one or more leads 424, and delivers each of the neurostimulation pulses through a set of electrodes selected from the electrodes 406. The stimulation output circuit 212 can implement, for example, the generating and delivery of a customized neurostimulation waveform (e.g., implemented from a parameter of a selected or specified program) to an anatomical target of a patient.

The stimulation control circuit 514 represents an embodiment of the stimulation control circuit 214 and controls the delivery of the neurostimulation pulses using the plurality of stimulation parameters specifying the pattern of the neurostimulation pulses. In one embodiment, the stimulation control circuit 514 controls the delivery of the neurostimulation pulses using the one or more sensed physiological signals and processed input from patient feedback interfaces.

The implant telemetry circuit 534 provides the implantable stimulator 404 with wireless communication with another device such as a device of the external system 402, including receiving values of the plurality of stimulation parameters from the external system 402. The implant storage device 532 stores values of the plurality of stimulation parameters, including parameters from one or more programs which are activated, de-activated, or modified using the approaches discussed herein.

The power source 536 provides the implantable stimulator 404 with energy for its operation. In one embodiment, the power source 536 includes a battery. In one embodiment, the power source 536 includes a rechargeable battery and a battery charging circuit for charging the rechargeable battery. The implant telemetry circuit 534 may also function as a power receiver that receives power transmitted from external system 402 through an inductive couple.

In various embodiments, the sensing circuit 530, the stimulation output circuit 212, the stimulation control circuit 514, the implant telemetry circuit 534, the implant storage device 532, and the power source 536 are encapsulated in a hermetically sealed implantable housing. In various embodiments, the lead(s) 424 are implanted such that the electrodes 406 are placed on and/or around one or more targets to which the neurostimulation pulses are to be delivered, while the implantable stimulator 404 is subcutaneously implanted and connected to the lead(s) 424 at the time of implantation.

Figure 6:
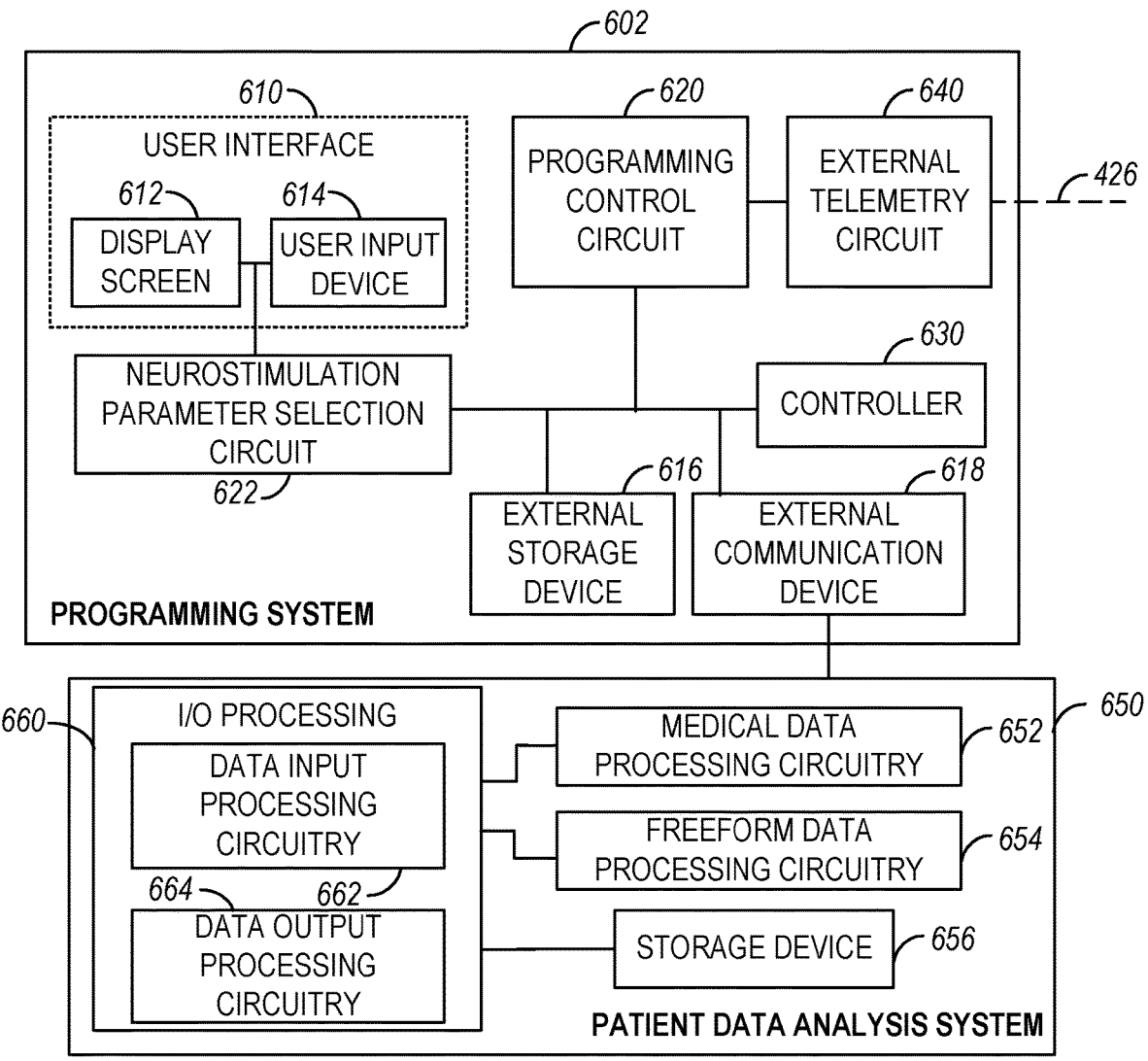
FIG. 6 illustrates, by way of example, an embodiment of a programming system and patient data analysis system for use with a neurostimulation system, such as the implantable neurostimulation system of FIG. 4.

FIG. 6 illustrates an embodiment of a programming system 602 used as part of an implantable neurostimulation system, such as the external system 402, with the programming system 602 configured to send and receive device data (e.g., commands, parameters, program selections, information). FIG. 6 also illustrates an embodiment of a patient data analysis system 650, communicatively coupled to the programming system 602. The patient data analysis system 650 is used to perform data analysis on freeform input (e.g., freeform text or audio converted to text) and device data in connection with neurostimulation treatment by the implantable neurostimulation system.

The programming system 602 represents an embodiment of the programming device 302, and includes an external telemetry circuit 640, an external storage device 616, a programming control circuit 620, a user interface device 610, a controller 630, and an external communication device 618, to effect programming of a connected neurostimulation device. The operation of the neurostimulation parameter selection circuit 622 enables selection, modification, and implementation of a particular set of parameters or settings for neurostimulation programming (e.g., via selection of a program, specification by a closed-loop or open-loop programming process, specification by a patient or clinician, or the like).

The external telemetry circuit 640 provides the programming system 602 with wireless communication to and from another controllable device such as the implantable stimulator 404 via the telemetry link 426, including transmitting one or a plurality of stimulation parameters (including selected, identified, or modified stimulation parameters of a selected program) to the implantable stimulator 404. In one embodiment, the external telemetry circuit 640 also transmits power to the implantable stimulator 404 through inductive coupling.

The external communication device 618 may provide a mechanism to conduct communications with a programming information source, such as a data service, program modeling system, to receive program information, settings and values, models, functionality controls, or the like, via an external communication link (not shown). In a specific example, the external communication device 618 communicates with the patient data analysis system 650 to identify parameters or settings that are selected, modified, or implemented in the neurostimulation programming. The external communication device 618 may communicate using any number of wired or wireless communication mechanisms described in this document, including but not limited to IEEE 802.11 (Wi-Fi), Bluetooth, Infrared, and like standardized and proprietary wireless communications implementations. Although the external telemetry circuit 640 and the external communication device 618 are depicted as separate components within the programming system 602, the functionality of both of these components may be integrated into a single communication chipset, circuitry, or device.

The external storage device 616 stores a plurality of existing neurostimulation waveforms, including definable waveforms for use as a portion of the pattern of the neurostimulation pulses, settings and setting values, other portions of a program, and related treatment information. In various embodiments, each waveform of the plurality of individually definable waveforms includes one or more pulses of the neurostimulation pulses, and may include one or more other waveforms of the plurality of individually definable waveforms. Examples of such waveforms include pulses, pulse blocks, pulse trains, and train groupings, and programs. The existing waveforms stored in the external storage device 616 can be definable at least in part by one or more parameters including, but not limited to the following: amplitude, pulse width, frequency, duration(s), electrode configurations, total charge injected per unit time, cycling (e.g., on/off time), waveform shapes, spatial locations of waveform shapes, pulse shapes, number of phases, phase order, interphase time, charge balance, and ramping.

The external storage device 616 may also store a plurality of individually definable fields that may be implemented as part of a program. Each waveform of the plurality of individually definable waveforms is associated with one or more fields of the plurality of individually definable fields. Each field of the plurality of individually definable fields is defined by one or more electrodes of the plurality of electrodes through which a pulse of the neurostimulation pulses is delivered and a current distribution of the pulse over the one or more electrodes. A variety of settings in a program may be correlated to the control of these waveforms and definable fields.

The programming control circuit 620 represents an embodiment of a programming control circuit 316 and may translate or generate the specific stimulation parameters or changes which are to be transmitted to the implantable stimulator 404, based on the results of the neurostimulation parameter selection circuit 622. The pattern may be defined using one or more waveforms selected from the plurality of individually definable waveforms (e.g., defined by a program) stored in an external storage device 616. In various embodiments, the programming control circuit 620 checks values of the plurality of stimulation parameters against safety rules to limit these values within constraints of the safety rules. In one embodiment, the safety rules are heuristic rules.

The user interface device 610 represents an embodiment of the user interface device 310 and allows the user (including a patient or clinician) to provide input relevant to therapy objectives, such as to switch programs or change operational use of the programs. The user interface device 610 includes a display screen 612, a user input device 614, and may implement or couple to the neurostimulation parameter selection circuit 622, or data provided from the patient data analysis system 650. The display screen 612 may include any type of interactive or non-interactive screens, and the user input device 614 may include any type of user input devices that supports the various functions discussed in this document, such as a touchscreen, keyboard, keypad, touchpad, trackball, joystick, and mouse. The user interface device 610 may also allow the user to perform other functions where user interface input is suitable (e.g., to select, modify, enable, disable, activate, schedule, or otherwise define a program, sets of programs, provide feedback or input values, or perform other monitoring and programming tasks). Although not shown, the user interface device 610 may also generate a visualization of such characteristics of device implementation or programming, and receive and implement commands to implement or revert the program and the neurostimulator operational values (including a status of implementation for such operational values). These commands and visualization may be performed in a review and guidance mode, status mode, or in a real-time programming mode. Consistent with the examples provided herein, the user interface device 610 may also allow the entry of unstructured, freeform data for collection and analysis using the processes discussed herein (e.g., with reference to FIGS. 7 to 12).

The controller 630 can be a microprocessor that communicates with the external telemetry circuit 640, the external communication device 618, the external storage device 616, the programming control circuit 620, the parameter selection circuit, and the user interface device 610, via a bidirectional data bus. The controller 630 can be implemented by other types of logic circuitry (e.g., discrete components or programmable logic arrays) using a state machine type of design. As used in this disclosure, the term "circuitry" should be taken to refer to discrete logic circuitry, firmware, or to the programming of a microprocessor.

The patient data analysis system 650 is configured to operate input/output processing circuitry 660, which may produce or initiate certain actions on based on freeform data (e.g., received and processed by freeform data processing circuit 654) and medical data (e.g., received and processed by medical data processing circuit 652). The input/output processing circuitry 660 may identify one or more patient states related to the neurostimulation treatment, using data input processing circuitry 662 to analyze the freeform data and the medical data. The input/output processing circuitry 660 may also provide outputs to a patient, a clinician, or other entity, based on the results of processing the freeform data and the associated medical data. Such outputs may include the storage or persistence of data, or other actions taken based on the detection of particular patient or device states from the freeform data.

The patient data analysis system 650 also is depicted as including a storage device 656 to store or persist data related to the freeform input, medical data, device data, patient or clinician output, and related settings, logic, or algorithms. Other hardware features of the patient data analysis system 650 are not depicted for simplicity, but are suggested from functional capabilities and operations in the following figures.

As will be understood, patients who are undergoing neurostimulation treatment may wish to provide detailed information regarding their current treatment and medical state within unstructured data fields, such as by supplying freeform text. Freeform text may take the form of a narrative, an explanatory statement, an answer to a question, key phrases, notes and observations, or the like. Such content may be quickly or easily supplied by the patient (or by a clinician who is overseeing the patient's care) and can provide many details regarding a patient's physiological and physiological state especially as conditions change during the neurostimulation treatment. However, unstructured data such as freeform text can be time-consuming or difficult to interpret and record, and even more difficult to turn into actionable data points.

As a complication to the collection of such unstructured data, a patient or clinician may provide information that is personally identifying (e.g., patient names or identifiers), or that is restricted by regulation (e.g., privacy or health data laws) or irrelevant to the neurostimulation treatment. This raises a number of operational and technical issues when identifying and storing relevant data, particularly in scenarios such as in clinical trials or patient studies where a large volume of patient feedback is collected for later analysis.

Prior approaches for obtaining feedback about a neurostimulation treatment or outcome often would involve the use of constrained inputs such as fixed survey fields that only obtain a limited set of answers from a patient. Such constrained inputs often fail to capture the nuance and the significance of historical events, and do not capture the surrounding context that is occurring from a patient. In contrast, the following approaches provide a system which can efficiently and quickly interpret freeform text, identify relevant conditions and patient state based on the interpreted text, redact or remove personally identifying information (or other private, and irrelevant information), and compile data to be used in connection with diagnosis, treatment, and remediation of neurostimulation programming and neurostimulation device operation.

Figure 7:
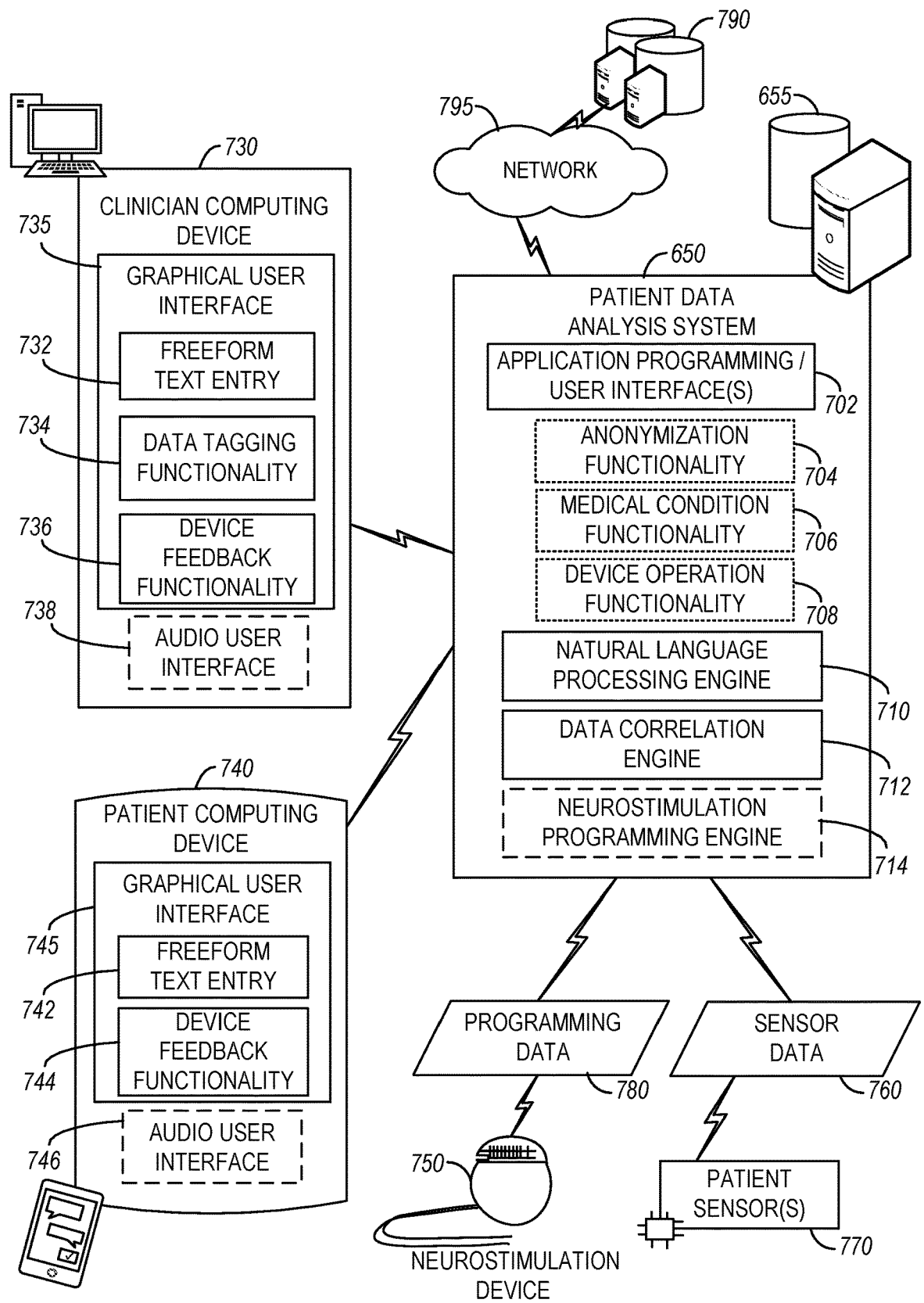
FIG. 7 illustrates, by way of example, an embodiment of data interactions among systems used for the collection and processing of relevant freeform patient data and neurostimulation data.

FIG. 7 illustrates, by way of example, an embodiment of data interactions among the patient data analysis system 650, a clinician computing device 730, and a patient computing device 740, for the collection and processing of relevant freeform patient data and neurostimulation data. Here, such data is being collected and processed for a patient being treated with neurostimulation via a neurostimulation device 750.

At a high level, the patient data analysis system 650 identifies characteristics of the neurostimulation treatment for a patient based on the analysis of freeform text provided from a clinician computing device 730 or patient computing device 740. The patient data analysis system 650 identifies and processes this freeform text using a natural language processing engine 710 and associates characteristics determined from the freeform text with a patient state or other medical data using a data correlation engine 712. The freeform text and medical data, in combination, may provide useful information on the past or current operation of the neurostimulation device 750, and optionally affect future operation of the neurostimulation device 750. The characteristics that are identified and correlated may be stored in local storage (e.g., database 655, maintained on storage device 656) or in remote storage (e.g., remote system 790 connected via network 795).

The patient data analysis system 650 includes a number of programmed functionality components to interpret and convert patient data, and in particular, to identify treatment characteristics from unstructured data relating to the patient. These programmed functionality components include anonymization functionality 704 (e.g., implementing algorithms and/or rules to redact, remove, or de-identify information from unstructured data that may be personally identifying), medical condition functionality 706 (e.g., implementing algorithms and/or rules to identify characteristics about the medical state of the patient, such as relating to pain), and a device operation functionality 708 (e.g., implementing algorithms and/or rules to identify the state of the neurostimulation device 750 and related programming). Such functionality may be coordinated with the use of the natural language processing (NLP) engine 710 to identify such characteristics from freeform text input. The analysis of text input with the NLP engine 710 may occur using one or more forms of keyword or phrase matching, text parsing, semantic and linguistic analysis, and the like.

The data (e.g., freeform text) may be received via an interface of the patient data analysis system 650, such as provided from an application programming interface or user interface 702. The text input also may be provided from other communications with the clinician computing device 730, the patient computing device 740, or third party devices and platforms not depicted. An example user interface from an implementation of a patient computing device 740 is provided in FIG. 8, discussed below, and additional workflows which invoke the use of the functionality 704, 706, 708 is discussed with reference to the user interfaces of FIGS. 9, 10A, and 10B, discussed below.

The patient data analysis system 650 also operates data correlation engine 712 to correlate (e.g., identify, match, associate) device state data and patient state data, collected from among multiple sources. The data correlation may be used to determine values of tags and other attributes. The use of tagging and the association of particular treatment characteristics with unstructured data is discussed in the examples below.

Finally, the patient data analysis system 650 optionally includes a neurostimulation programming engine 714 to evaluate or determine operational conditions of programming for the neurostimulation device 750. In an example, the neurostimulation programming engine 714 enables control, modification, selection, or specification of neurostimulation programming parameters, in an automatic, suggested, or manual fashion, such as based on conditions identified after analyzing the freeform input. Additional detail regarding programming or control of the device 750 based on the freeform input is provided in the example of FIG. 11, below, but it will be understood that other embodiments of program modeling, selection, recommendation, and implementation may be provided via programming devices, data services, or information services which are not depicted.

In an example, the patient computing device 740 is a computing device (e.g., personal computer, tablet, smartphone) or other user-operated device which receives and provides interaction with a patient using a graphical user interface 745 and optionally an audio user interface 746. Within the graphical user interface 745, input functionality is provided through a freeform text entry functionality 742 and device feedback functionality 744. For instance, the freeform text entry functionality 742 may receive freeform text entered by a patient via a text box, answer fields, surveys, messages, or other textual inputs. The device feedback functionality 744 may be used to provide outputs that indicate whether the input being provided is valid or will be redacted, and to allow the user to specify additional details or resolve ambiguous information.

The clinician computing device 730 likewise may be a computing device which implements a graphical user interface 735 and optionally an audio user interface 738. The features of the graphical user interface 735 may offer similar capabilities to the graphical user interface 745 provided for the patient, but adapted for use by a clinician (e.g., to provide enhanced functionality or features for physician control and input). Here, the functionality may include freeform text entry 732, data tagging functionality 734, and device feedback functionality 736. The data tagging functionality 734 may allow enhanced features to allow tags to be specified by a clinician directly in freeform text or to be selected based on the entry of freeform text, consistent with the examples below.

The patient data analysis system 650 also may utilize sensor data 760 from one or more patient sensors 770 (e.g., wearables, sleep trackers, motion tracker, implantable devices, etc.) among one or more internal or external devices. The sensor data 760 may provide medical data to determine a customized and current state of the patient condition or neurostimulation treatment results, to be correlated with freeform text information. In various examples, the neurostimulation device 750 includes sensors which contribute to the sensor data 760 evaluated by the patient data analysis system 650.

In an example, the patient sensors 770 are physiological or biopsychosocial sensors that collect data relevant to physical, biopsychosocial (e.g., stress and/or mood biomarkers), or physiological factors relevant to a state of the patient. Examples of such sensors might include a sleep sensor to sense the patient's sleep state (e.g., for detecting lack of sleep), a respiration sensor to measure patient breathing rate or capacity, a movement sensor to identify an amount or type of movement, a heart rate sensor to sense the patient's heart rate, a blood pressure sensor to sense the patient's blood pressure, an electrodermal activity (EDA) sensor to sense the patient's EDA (e.g., galvanic skin response), a facial recognition sensor to sense the patient's facial expression, a voice sensor (e.g., microphone) to sense the patient's voice, and/or an electrochemical sensor to sense stress biomarkers from the patient's body fluids (e.g., enzymes and/or ions, such as lactate or cortisol from saliva or sweat). Other types or form factors of sensor devices may also be utilized.

Figure 8:
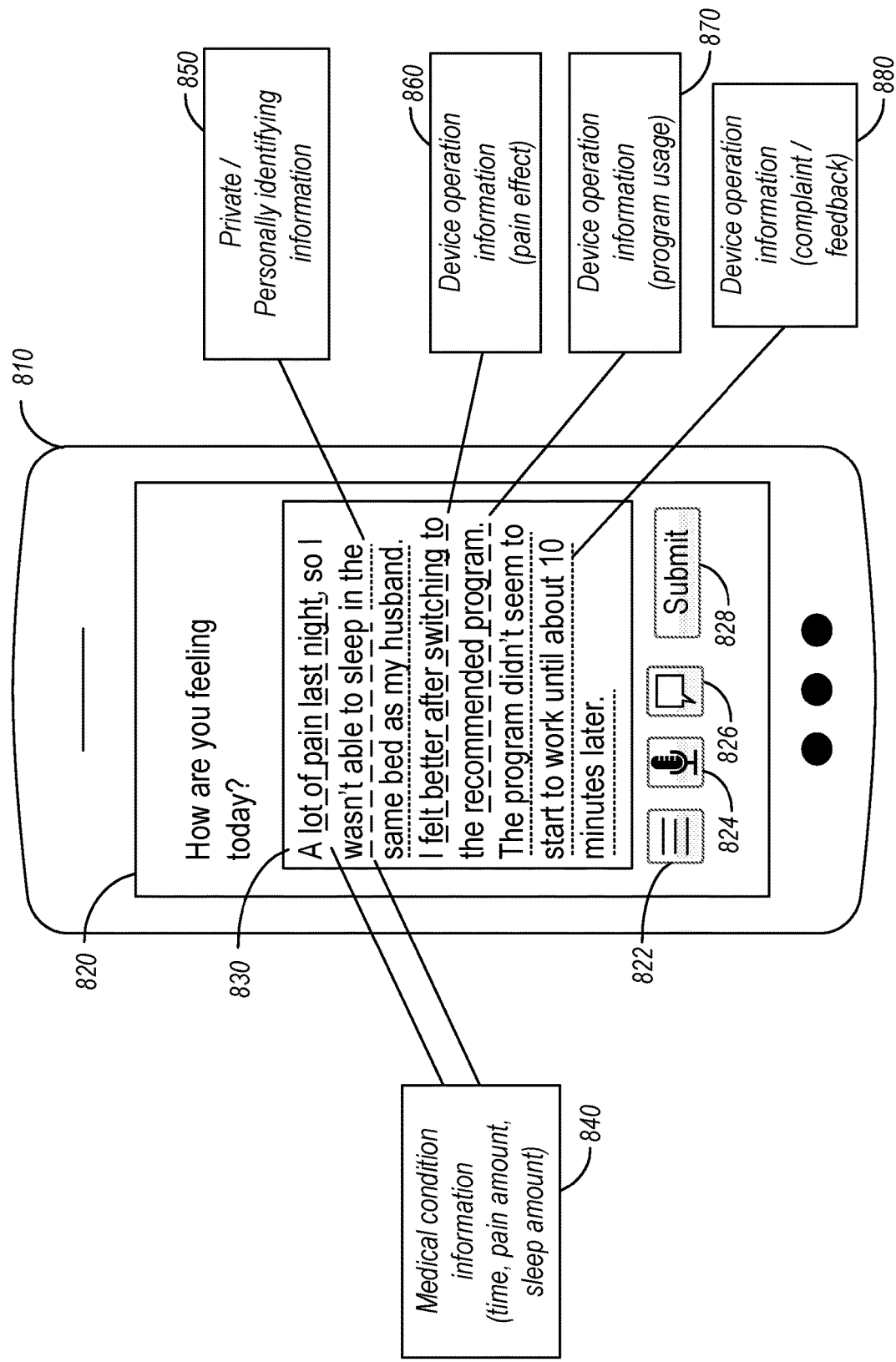
FIG. 8 illustrates, by way of example, a user interface for receiving unstructured text from a human patient.

FIG. 8 illustrates a user interface 820 configured for receiving unstructured text (textual input) from a human patient. Specifically, the user interface 820 depicted in FIG. 8 demonstrates the use of a graphical user interface to collect freeform text replies, entered in response to a question posed to the patient. It will be understood that the user interface 820 provides a high level illustration of possible functionality, and does not fully depict all functions or features which may be provided in a text entry user interface.

In additional detail, the user interface 820 is depicted as operating on a mobile computing device 810, such as in the form of an interactive software "app" which receives commands and interaction via touchscreen commands. The user interface 820 also includes user interface functionality such as in the form of a keyboard control 822 (e.g., to toggle, invoke, or control an on-screen keyboard), a speech input control 8224 (e.g., to toggle, invoke, or control entry of audio content provided by user speech, such as though a microphone of the mobile computing device 810), and a conversation control 826 (e.g., to present an interactive mode to invoke a conversation, such as with a series of questions from a chatbot, script, or organized dialogue). A "submit" button user interface control 828 is also provided to allow the user to submit the data for further processing (including redaction, tagging, and identification of relevant data features).

The text entered into text field 830 is unstructured, freeform text, which provides a number of keywords, terms, and phrases that are either relevant or non-relevant to a neurostimulation treatment. For instance, a first portion of the entered text includes keywords and phrases relevant to medical condition information 840 (e.g., indicating that the patient was in "a lot of pain last night", and the patient "wasn't able to sleep"). This medical condition information 840 may indicate attributes relevant to time, an amount of a condition (e.g., pain amount), an amount of a related condition (e.g., sleep amount). Other attributes may also be indicated that are relevant to a medical condition of the patient.

The second portion of the entered text includes characteristics that qualify as private or personally identifying information 850. As an example, such information may indicate some personal characteristic of the patient, such as marital or relationship status, the name of the patient, the name of the patient's doctor, an identifier associated with the patient or a medical facility which treats the patient, or the like. It will be understood that a variety of other information may constitute private or personally identifying information 850, including information that is protected by privacy or health regulations or laws.

The third portion of the entered text includes characteristics which qualify as device operation information, including information 860 indicating a pain effect ("felt better") from use of the neurostimulation, and information 870 indicating usage of a specific program for the neurostimulation (the "recommended program"). This information 860, 870 may be matched and associated with device settings or device programming programs, depending on the context indicated by the information 860, 870 and meaning of the text in the information 860, 870 and surrounding sentences.

The fourth portion of the entered text includes characteristics which qualify as another form of device operation information, including information 880 which provides a complaint or feedback regarding usage of the device. Here, this information 880 can be processed to identify a possible error or operational issue with the device (i.e., whether the program was successfully activated or delayed). This information 880 may be logged and flagged for further review by a clinician or a support personnel depending on the context indicated by the information 880 and meaning of the text in the information 880 and surrounding sentences.

The information that is obtained in the interactions of user interfaces may be collected and analyzed from a single or multiple interactions with the patient or clinician. For instance, such analysis may be used to determine whether the result of some neurostimulation program or setting is currently or was previously beneficial to treatment and the patient state. As different interactions occur, data may be analyzed to track a particular state of a patient at a particular time, and the progression of the patient over time, such as by comparing the appearance of various keywords or terms in the freeform text. At a simple example, this might be implemented by the occurrence of particular keywords (e.g., how many times and when "less pain" occurs), or by scoring applied to determine the meaning of the text (e.g., with sentiment analysis or other natural language processing techniques). It will be understood that a variety of algorithms may be used to identify and track the meanings of keywords and phrases.

Figure 9:
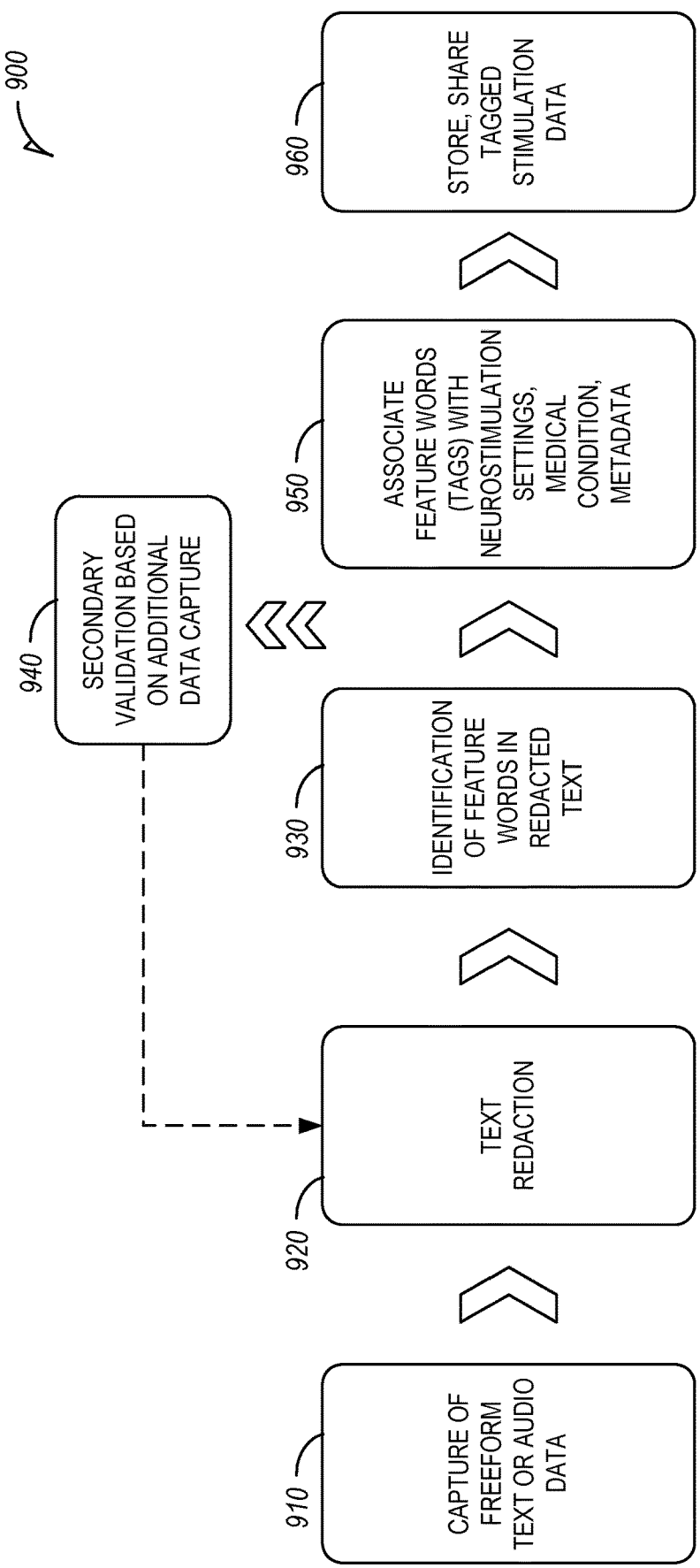
FIG. 9 illustrates, by way of example, a sequence of data processing operations performed on freeform text or audio data.
Figure 10:
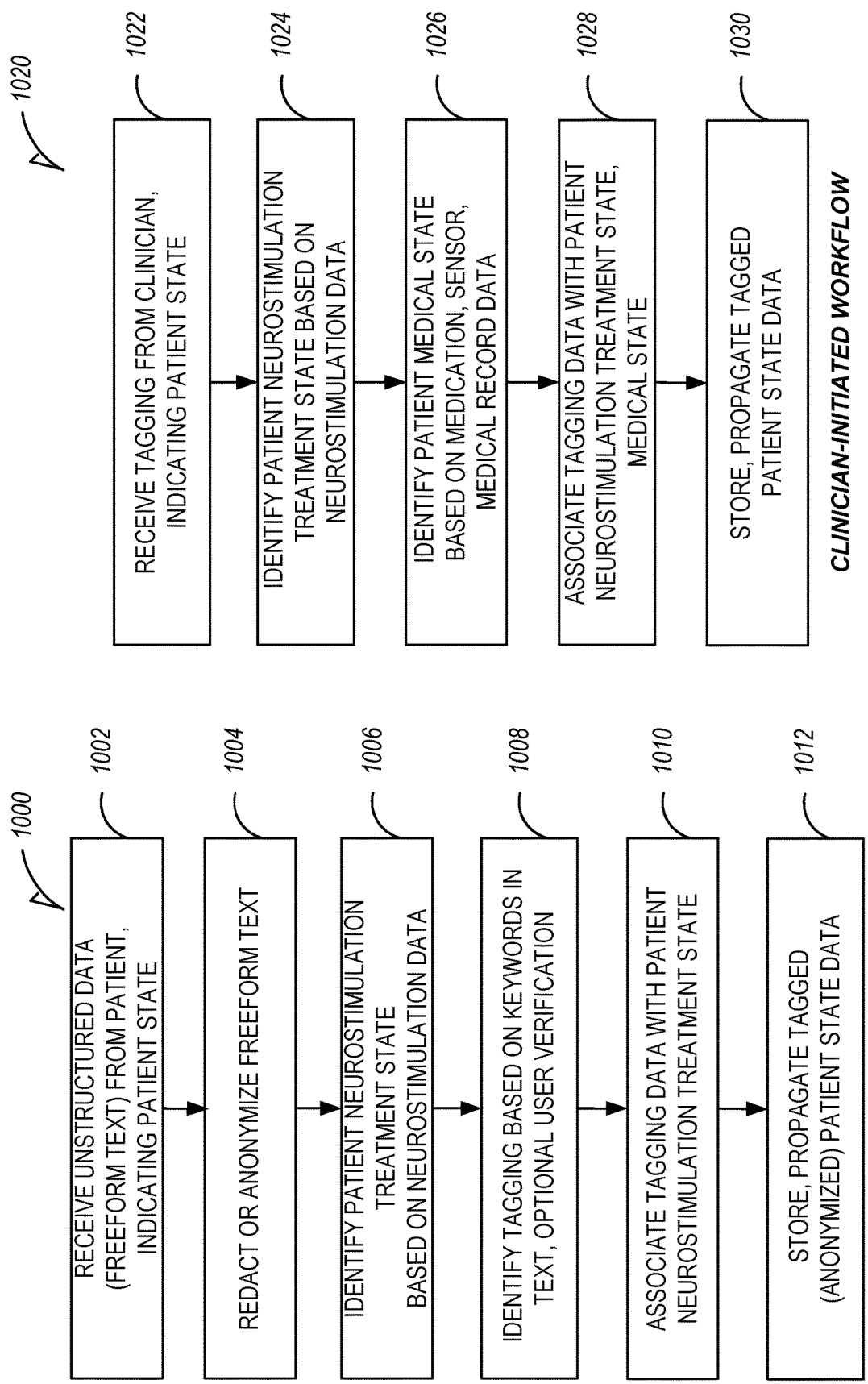
FIGS. 10A and 10B illustrate, by way of example, flowchart workflow sequences of the collection and processing of textual input from a patient and from a clinician, respectively.

FIG. 9 illustrates, by way of example, a sequence of data processing operations 900 performed on freeform text or audio data, such as entered with the user interfaces 735, 745, or 820. In particular, the data processing operations 900 present an example approach of how particular keywords ("feature words") can be identified from freeform input, even though the freeform input may also include other words and private (personal) or irrelevant content.

In the data processing operations 900 of FIG. 9, the freeform input (provided as text or audio data) is captured at operation 910. Such freeform input, if captured as audio, may be converted into text with a speech-to-text engine. The text provided from the freeform input is redacted at operation 920. This redaction may occur with the use of rules, such as rules that allow (include) certain words, exclude certain words, and redact or replace certain words. The redaction may occur with the use of algorithms or language processing models. Such redaction may produce text data which is suitably anonymized and de-identified.

At operation 930, an identification of "important" feature words is performed on the redacted text. This may include the review of particular terms relevant to neurostimulation, such as to search and flag one or more words, terms, or phrases which indicate concepts such as "Off Medication" or "On Medication" or synonyms of these keywords. In some examples, a library of keywords (and variations of these keywords) is used for word recognition, consistent with the discussion of "allowed", "excluded", and "redacted" word lists below.

At operation 940, an operational operation for validation is performed, based on the recognized keywords or terms. This may include the use of a secondary validation workflow that is presented to the user, to allow the user to provide additional, supplemental, or clarifying data. The secondary validation workflow may be provided in the form of user interface prompt (e.g., pop-up screen, additional question, etc.) which asks for additional information from the user. The additional data captured from this workflow may be provided for use in operations 920 and 930, or directly to proceed with operation 950.

At operation 950, feature words which are identified are associated with relevant neurostimulation settings and data. This has the effect of establishing data "tags" to be associated with the freeform text. The data tags may associate information such as neurostimulation settings (e.g., which program was used), medical condition data (e.g., type and status of medication), and metadata (e.g., time and date associated with the neurostimulation or medical condition, or identification of the text entry user). As an example, a "Off Medication" tag, determined from the detection of feature keywords, may be associated with a current stimulation setting (e.g., to identify a program) and the current date, time, and data entry user (e.g., whether a physician, patient, representative).

At operation 960, the tagged stimulation data may be stored and shared with relevant downstream entities. For example, all stimulation data tagged with the "Off Medication" tag and associated metadata can be shared or used for further processing. This may include, sharing and providing such data to relevant users, other software applications, algorithms, services and databases.

Other operations (not depicted in the workflow of FIG. 9) may include the collection of user approval to assist the redaction of text at operation 920, to assist the identification of feature words at operation 930, to assist the association of feature words with metadata or other information at operation 950, or to obtain express approval to allow the sharing of stimulation data at operation 960. For instance, after entry of the freeform text, the user may be provided with a selectable option (e.g., activated via a button) to preview what the redacted entry will look like when shared to another device. This may allow the user to verify the data to ensure that the meaning of the redacted text remains accurate. Other functionality be implemented in connection with user approval. For example, the user may can choose to change what is written (and review the redacted text again), or select additional words to be redacted. The user may also specify information to prevent sharing of the data with certain devices or systems.

As an example of the redaction rules applied at operation 920 and the word identification process applied at operation 930, the system may apply the following criteria.

Identification of Allowed words/phrases: The system may be programmed with an extensive list of approved words/phrases to allow, including common words (e.g., is, the, are, a, etc.) as well as those that are disease specific (e.g., bradykinesia, tremor, dysarthria). These words will be allowed to be maintained in the text input.

Identification of Excluded words/phrases: The system may be programmed with an extensive list of words to exclude (e.g., omit, remove), including common names of hospitals, clinics, and individuals. The system may also include logic to exclude all numbers, whether written out in text or in numerals. The system may also exclude dates, references to months, or other time/date attributes.

Identification of Redacted words/phrases: Words/phrases are not on the Allowed list or the Excluded list are identified as words to be redacted. Such words or phrases may be designated to not be visible within the text, outside of the system on which they were entered. In an example, redacted words/phrases (except for words on the Excluded list) can be sent to a common database.

In an example, all Redacted words or phrases will be separated from the surrounding text and have no connection to any other patient related information, creating an isolated word cloud. Once a sufficient portion of data has been collected, this word cloud can be analyzed for top occurring words across entries. Words that are Redacted but not on the Excluded list can also be ranked. Top ranked words can either be entered into the Allowed or Excluded word list (for instance, commonly redacted words may be used to capture common misspellings). The Allowed and Excluded word lists can then be updated in the system to improve usability.

As will be understood, various functionality may be designed to allow the expansion and adoption of updated word lists, to update the listings of Redacted, Allowed, and Excluded words, noted above. Following approval of a new word list, previously entered text may require user approval before being reshared with the new redaction rules.

Other adaptation of the text processing techniques above may be provided, based on the type of text being entered or the algorithms, logic, or processes used to process the text. This may include the support of multiple languages, conversion among languages, or other transformations of the text from one format or form to another.

As noted above, the processing of freeform text may be assisted by various tagging scenarios which associate the text with particular patient states or treatment attributes. Such tagging may be automatically determined from keywords provided in the freeform text, or by tags that are associated with the text.

For example, consider a scenario where information from deep brain stimulation is logged. In connection with a deep brain stimulation treatment, the medication state of the patient may be relevant to determine whether the stimulation is providing useful treatment. Thus, the patient's observed clinical effects are suspected to shift when the patient is in an "on-medication" or an "off-medication" set. In an example using automatic tagging, a physician enters freeform data to record the state of the patient treatment, using words or keywords such as "Meds Off Initial Programming." The system identifies the keyword "Meds Off", and determines a "Off Medication" tag is relevant to the freeform text and associated programming data. All stimulation data collected from the programming session is then tagged with the "Off Medication" tag within an internal data structure (even in scenarios where there is not a selectable option in the user interface to indicate this property). In another example that supports user-assisted tagging, the "Off Medication" tag may be automatically generated or obtained from a user approval prompt. For example, as a user (clinician) enters data, the user may be asked whether they would like all associated neurostimulation data to be tagged with the "Off Medication" tag.

Additionally, consider another scenario where information from spinal cord stimulation is logged. The remote control for the spinal cord stimulation system includes a free entry text field that is used to collect text on the patient's status. The patient states that they have "No numbness after changing programs yesterday." In this example, the keyword "numbness" and the phrase "no numbness" can be processed to determine that this is relevant to a state of no paresthesia. A tag of "Paresthesia Free" can be associated with the current neurostimulation program automatically, or the user can be prompted by an additional questionnaire to affirmatively answer if they are feeling any numbness or tingling with the current neurostimulation settings. The user's answer to this question can also be used to provide verification before the tag "Paresthesia Free" can be applied to the neurostimulation setting. In addition to the tag "Paresthesia Free", metadata can be associated with this tag, such as an indication of which user entered the data patient, caregiver, physician, or medical device representative), and a date and time associated with the data entry. As will be understood, this type of metadata allows additional tracking of information that may be relevant to care, but that is not generally logged or captured by freeform text entries.

If tagging results are not directly verified by an individual (such as a patient or physician) that entered the data, the tagging data may be identified as automatically generated or unverified. For example, particular tags or tagging data may be labeled as being derived based on user entry.

The use of automatic or user-assisted tagging may allow a variety of attributes to be identified and associated with other neurostimulation data values. The use of tagging allows data being stored on the device, programmer, or programming system to remain unchanged, while allowing downstream databases and other applications to derive additional information from the collected freeform and neurostimulation data. It will be understood that tagged data can be forwarded to a variety of other entities for further use and processing. For instance, tagged data may be provided (e.g., communicated, forwarded, granted access rights) to a clinician, patient representative, caregiver, or other parties. Tagged data may also be provided to other downstream algorithms for further analysis and verification.

FIGS. 10A and 10B illustrate, by way of example, detailed workflow sequences 1000, 1020 of how textual input may be provided by a patient or clinician respectively, and used for tagging and associating particular data attributes with freeform input. Although sequences 1010, 1020 are depicted as separate workflows, it will be understood that aspects of the sequences may be combined or integrated with either other, or, into the processing method 1200 of FIG. 12, discussed below.

The sequence 1000 details a process for a patient-initiated (or caregiver-initiated) workflow, beginning with operations to receive unstructured data, such as freeform text (or freeform audio narration to be converted into text), which includes information about the patient state (operation 1002). Such information may be entered by any person who has permission to provide information about the patient, such as a family member caregiver, home health caregiver, patient representative from a medical device company, etc. Based on the keywords and terms used in this freeform text, operations are performed to redact private information or anonymize the freeform text (operation 1004).

Additional operations are performed to identify the patient neurostimulation treatment state, and metadata associated with the neurostimulation treatment state, based on neurostimulation data (operation 1006). The workflow continues with the identification of tags and performing tagging based on keywords identified from the text (operation 1008), and optionally, user verification. The workflow continues with the association of tagging data (tags) with a patient neurostimulation treatment state (operation 1010). The workflow concludes with the storage and propagation of anonymized patient state data (operation 1012).

The sequence 1020 details a similar process for a medical professional (e.g., clinician)-initiated workflow, which may involve any number of medical professionals or authorized persons associated with the medical care or treatment (e.g., a medical device company representative, clinical research personnel, etc.). The sequence begins with operations to receive tagging from the medical professional, indicating a patient state (operation 1022). A patient neurostimulation treatment state is identified based on neurostimulation data (operation 1024) and a patient medical state is identified based on medical data available to the clinical practice or associated with the medical care, such as medication data, sensor data, or medical record data (operation 1026). The workflow continues with the association of tagging data (tags) with a patient neurostimulation treatment state and medical state (operation 1028). The workflow concludes with the storage and propagation of anonymized patient state data (operation 1012).

Although the prior examples discussed collection of text in user interfaces, other types of unstructured information may be collected in a variety of forms from electronic interactions. Other example implementations may be provided by other types of textual or verbal interactions, such as via electronic messaging, chat sessions, or recordings of human-agent interactions. Additionally, although many of the preceding approaches were discussed with reference to freeform text analysis, keyword identification and extraction/redaction, and natural language processing, these and other approaches may be supplemented or substituted with technical implementations involving artificial intelligence (AI), including with use of models that implement machine learning, neural networks, decision trees, and the like.

Based on the collection of the text data in such workflows, a variety of downstream actions may occur. This may include logging of the collected data, or further analysis of the collected data to determine immediate or future actions. This may also include the identifications of device technical issues based on complaints, or an identification of operations for clinical intervention, triage, device diagnostics, remediation, or logging.

Figure 11:
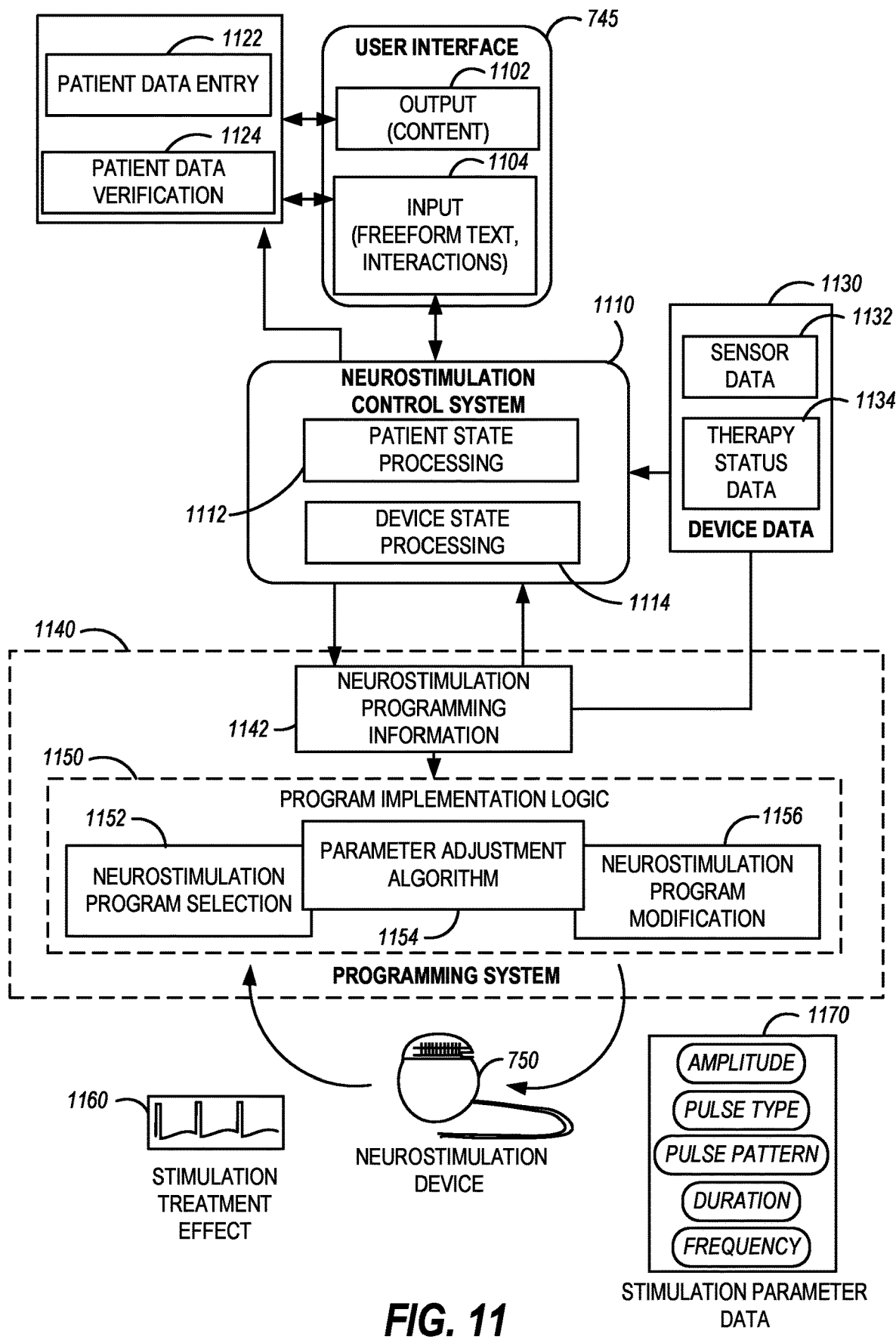
FIG. 11 illustrates, by way of example, a data processing flow for affecting the neurostimulation treatment of a human patient, based on freeform user input and data tagging.

FIG. 11 illustrates, by way of example, an embodiment of a data processing flow affecting the neurostimulation treatment of a human patient, which may occur in response to the freeform user input and data tagging operations discussed above. Specifically, this data processing flow shows how a neurostimulation control system 1110 may include patient state processing 1112 and device state processing 1114 functions, based on freeform text and tagging of the freeform text (discussed above) to control neurostimulation programming. Other user interfaces and actions are not depicted for simplicity.

In this example, input 1104 (e.g., freeform text, tags, other user interactions) is obtained by the user interface 745, as discussed above. The user interface 745 provides various patient data entry operations 1122 and patient data verification operations 1124, with use of input functionality 1104 and output functionality 1102. Such operations and functionality may be consistent with those discussed with reference to FIGS. 7 to 9.

FIG. 11 also depicts the evaluation of device data 1030, such as sensor data 1032, therapy status data 1034, and other treatment aspects which may be obtained or derived from the neurostimulation device 750 or related neurostimulation programming. The device data 1130 and the inputs received with the user interface 745 allow a patient state and device state to be determined within patient state processing functions 1112 and device state processing 1114.

The remainder of the data processing flow illustrates how the patient state and device state is used by the neurostimulation control system 1110 to effect programming, such as in a closed loop (or partially-closed-loop) system. A programming system 1140 uses programing information 1142 provided from the neurostimulation control system 1110 as an input to program implementation logic 1150. The program implementation logic 1150 may be implemented by a parameter adjustment algorithm 1154, which affects a neurostimulation program selection 1152 or a neurostimulation program modification 1156. For instance, some parameter changes may be implemented by a simple modification to a program operation; other parameter changes may require a new program to be deployed. The results of the parameter or program changes or selection provides various stimulation parameters 1170 to the neurostimulation device 750, causing a different or new stimulation treatment effect 1160.

By way of example, operational parameters of the neurostimulation device which may be generated, identified, or evaluated by the neurostimulation control system 1110 may include amplitude, frequency, duration, pulse width, pulse type, patterns of neurostimulation pulses, waveforms in the patterns of pulses, and like settings with respect to the intensity, type, and location of neurostimulator output on individual or a plurality of respective leads. The neurostimulator may use current or voltage sources to provide the neurostimulator output, and apply any number of control techniques to modify the electrical simulation applied to anatomical sites or systems related to pain or analgesic effect. In various embodiments, a neurostimulator program may be defined or updated to indicate parameters that define spatial, temporal, and informational characteristics for the delivery of modulated energy, including the definitions or parameters of pulses of modulated energy, waveforms of pulses, pulse blocks each including a burst of pulses, pulse trains each including a sequence of pulse blocks, train groups each including a sequence of pulse trains, and programs of such definitions or parameters, each including one or more train groups scheduled for delivery. Characteristics of the waveform that are defined in the program may include, but are not limited to the following: amplitude, pulse width, frequency, total charge injected per unit time, cycling (e.g., on/off time), pulse shape, number of phases, phase order, interphase time, charge balance, ramping, as well as spatial variance (e.g., electrode configuration changes over time). It will be understood that based on the many characteristics of the waveform itself, a program may have many parameter setting combinations that would be potentially available for use.

Figure 12:
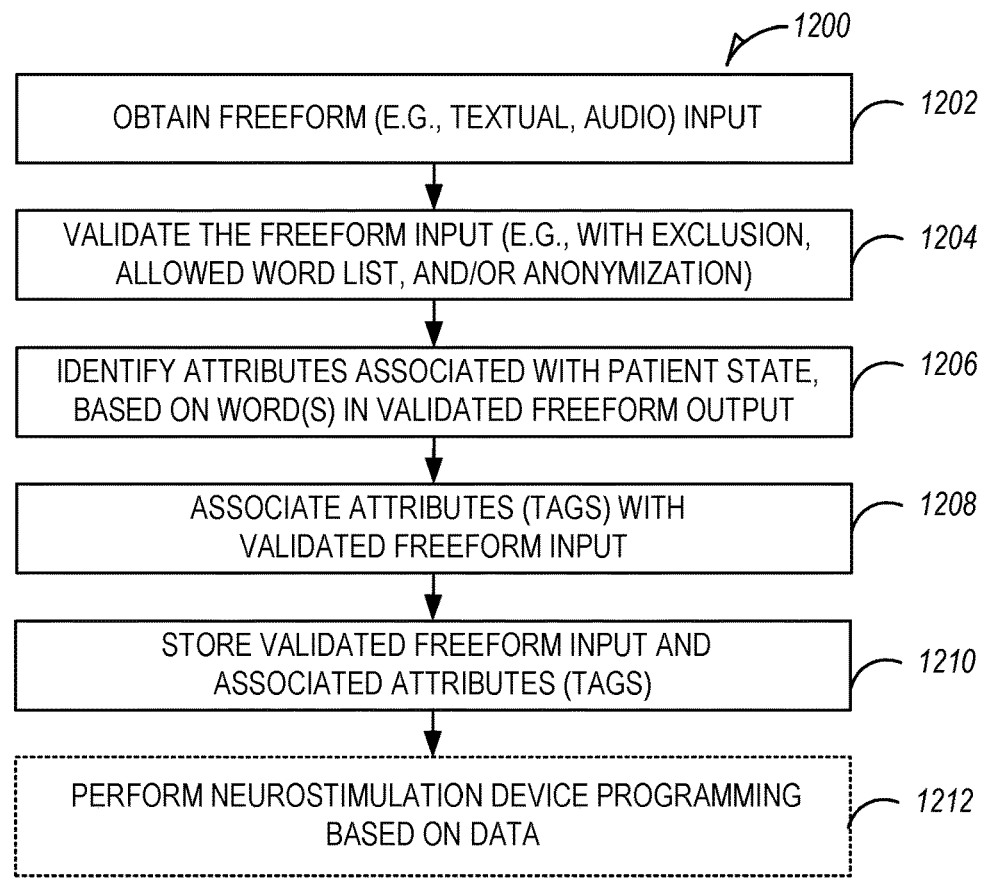
FIG. 12 illustrates, by way of example, a flowchart of a method implemented by a system or device to process freeform data relating to a neurostimulation treatment.

FIG. 12 illustrates, by way of example, an embodiment of a processing method 1200 implemented by a system or device for use to process freeform data relating to a neurostimulation treatment. For example, the processing method 1200 can be embodied by electronic operations performed by one or more computing systems or devices (including those at a network-accessible remote service) that are specially programmed to implement the data analysis and/or neurostimulation data processing operations described herein. In specific examples, the operations of the method 1200 may be implemented through the systems and data flows depicted above in FIGS. 6 to 11, at a single entity or at multiple locations.

In an example, the method 1200 begins by obtaining the freeform (e.g., textual or audio) input (operation 1202), such as is discussed above with reference to the examples of freeform text captured in FIG. 8, as well as other examples such as entry in a mobile device app, SMS or text/chat message interfaces, etc. Such freeform input may originate from the human patient, a caregiver, or a medical professional (e.g., clinician, medical device representative, researcher, etc.) associated with and/or authorized by the human patient. This freeform input may indicate, or relate to, one or more characteristics of a neurostimulation treatment of a human patient, or related conditions or states of the human patient. In various examples, such freeform input may originate from text directly entered into a text input field, or an audio input or audio recording converted to text.

The method 1200 continues with the validation of the freeform input (operation 1204), such as with the use of exclusion or allowed (inclusion) word lists, or redaction as discussed above. In a specific example relating to exclusion, validation of the freeform input includes operations to identify one or more words for exclusion in the freeform input, based on an exclusion word list, and then remove the one or more words for exclusion from the freeform input, to produce validated freeform input. This exclusion word list may be determined based on natural language processing of the freeform input (e.g., to normalize or de-duplicate similar forms of the same words or phrases). In a specific example relating to inclusion (which may be combined with the examples of exclusion), validation of the freeform input includes operations to identify one or more words for inclusion in the freeform input, based on an allowed word list, and then select the one or more words from the freeform input, to produce the validated freeform input. This allowed word list may be determined based on natural language processing of the freeform input (e.g., to normalize or de-duplicate similar forms of the same words or phrases).

In some examples, validation of the freeform input also includes or is followed by anonymization of the freeform input, to remove personally identifying information from the freeform input. Such anonymization may be based on personally identifying information, protected health information, or characteristics that are specific to a clinical evaluation, a research study, or specific project. For example, such anonymization in a research study setting may include removing information which may cause unblinding for blinded study investigators, for device manufacturer or support personnel, or other relevant entities associated with a study or investigation. In still a further example, validation of the freeform input also includes or is followed by user validation of the anonymized or redacted freeform input (e.g., to ask a user if they approve of sharing the redacted or anonymized information).

The method 1200 continues with the identification of one or more attributes associated with a patient state, based on one or more words identified in the validated freeform output (operation 1206). The particular patient state that is identified may include features, definition, or a relationship to at least one physiological condition identified from the validated freeform input. Such a physiological condition may be associated with (or causative of): pain measurements, pain states, sleep measurements, sleep states, movement, activity, mobility, physical function, cardiac function, autonomic function, medication, or emotional state, for the human patient. Other physiological conditions, values, measurements, or states may also be considered as part of the patient state.

The attributes that are associated with the patient state, as a result of words in the validated freeform output, may include the tags and tagging process discussed above. In an example, such attributes indicate (e.g., are based on, related to, or provide information of) a state of a medical condition and/or a state of the neurostimulation treatment for the human patient. These attributes may be identified using natural language processing of the one or more words from the validated freeform input. These attributes optionally may also be determined, verified, or matched with an identified state of the medical condition of the patient, such as an identified state determined from other medical data sources, such as from one or more of: medication data (from one or more medications), sensor data (from one or more sensors), or neurostimulation device data (from the subject neurostimulation device, or related systems). These attributes optionally may also be determined, verified, or matched with an identified state of the neurostimulation treatment (e.g., from past treatments of the patients), such as from one or more of: prior neurostimulation settings, current neurostimulation settings, or scheduled programmed neurostimulation settings. It will be understood that the one or more medications considered here may or may not be related to the use of the neurostimulation device or the treatment objectives of neurostimulation. Also, the one or more sensors providing data here may or may not be related to sensors of the neurostimulation device, implanted sensors, as other external sensors or devices may also provide data.

The method 1200 continues by associating the attributes (e.g., tags) with validated freeform input (operation 1208). In a particular example, such attributes may be used to associate a patient state (e.g., a patient condition or particular state indicated by the text) with the use or non-use of at least one neurostimulation program. Specifically, this may include matching use of at least one neurostimulation program (e.g., at a particular date and time) to the state of the human patient (e.g., some state indicated in the freeform text), based on a usage of the at least one neurostimulation program (e.g., used by a neurostimulation device implanted in the human patient).

The method 1200 continues to store the validated freeform input and associated attributes (e.g., tags) (operation 1210). For example, this may involve causing the data to be stored in a remote database (e.g., a research database or system) which maintains data (e.g., anonymized data) for a plurality of human patients which have undergone or are currently undergoing neurostimulation treatment. Such data and attributes may also be communicated to or further analyzed by other entities.

In further examples, the method 1200 continues with optional operations to perform a change in neurostimulation device programming, based on the analyzed freeform data (operation 1212). Such changes may occur immediately, at a later time, or as a result of additional analysis and verification. Such changes may enable a closed-loop or partially-closed-loop feedback system, to allow dynamic changes as a result of intuitive user written or verbal feedback.

Figure 13:
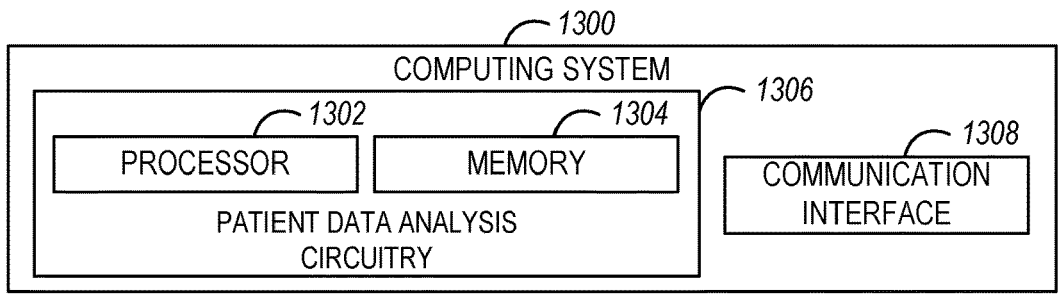
FIG. 13 illustrates, by way of example, a block diagram of an embodiment of a computing system for performing patient data analysis in connection with the freeform data processing operations discussed herein.

FIG. 13 illustrates, by way of example, a block diagram of an embodiment of a system 1300 (e.g., a computing system) for performing patient data analysis in connection with the freeform data processing operations discussed above. The system 1300 may be integrated with or coupled to a computing device, a remote control device, patient programmer device, clinician programmer device, program modeling system, or other external device, deployed with neurostimulation treatment. In some examples, the system 1300 may be a networked device (server) connected via a network (or combination of networks) which communicates to one or more devices (clients) using a communication interface 1308 (e.g., communication hardware which implements software network interfaces and services). The network may include local, short-range, or long-range networks, such as Bluetooth, cellular, IEEE 802.11 (Wi-Fi), or other wired or wireless networks.

The system 1300 includes a processor 1302 and a memory 1304, which can be optionally included as part of patient data analysis circuitry 1306. The processor 1302 may be any single processor or group of processors that act cooperatively. The memory 1304 may be any type of memory, including volatile or non-volatile memory. The memory 1304 may include instructions, which when executed by the processor 1302, cause the processor 1302 to implement freeform data processing, or to enable other features of the patient data analysis circuitry 1306. Thus, electronic operations in the system 1300 may be performed by the processor 1302 or the circuitry 1306.

For example, the processor 1302 or circuitry 1306 may implement any of the features of the method 1200 (such as operations 1202-1212) to obtain and process patient freeform input and device data, identify a state of a human patient and a state of the neurostimulation treatment, and perform data processing and storage based on such freeform input and identified state data. It will be understood that the processor 1302 or circuitry 1306 may also implement aspects of the logic and processing described above with reference to FIGS. 6-12, for use in various forms of closed-loop and open-loop device programming or related device actions.

Figure 14:
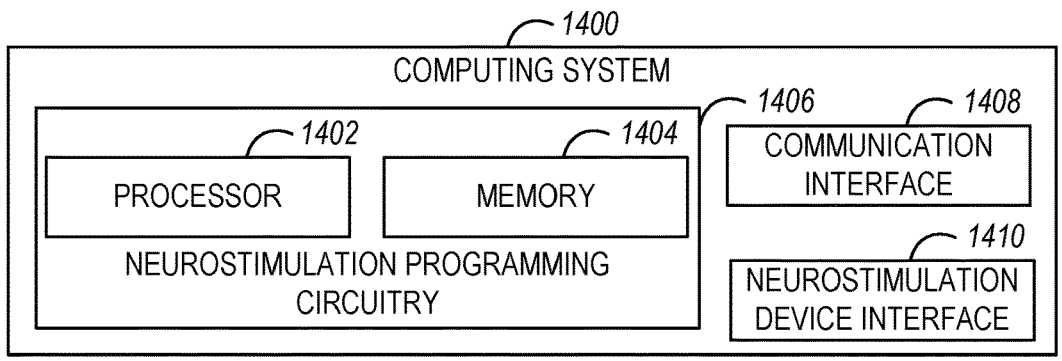
FIG. 14 illustrates, by way of example, a block diagram of an embodiment of a computing system implementing neurostimulation programming circuitry, to cause programming of an implantable electrical neurostimulation device.

FIG. 14 illustrates, by way of example, a block diagram of an embodiment of a system 1400 (e.g., a computing system) implementing neurostimulation programming circuitry 1406 to cause programming of an implantable electrical neurostimulation device, for accomplishing the therapy objectives in a human subject as discussed herein. The system 1400 may be operated by a clinician, a patient, a caregiver, a medical facility, a research institution, a medical device manufacturer or distributor, and embodied in a number of different computing platforms. The system 1400 may be a remote control device, patient programmer device, program modeling system, or other external device, including a regulated device used to directly implement programming commands and modification with a neurostimulation device. In some examples, the system 1400 may be a networked device connected via a network (or combination of networks) to a computing system operating a user interface computing system using a communication interface 1408. The network may include local, short-range, or long-range networks, such as Bluetooth, cellular, IEEE 802.11 (Wi-Fi), or other wired or wireless networks.

The system 1400 includes a processor 1402 and a memory 1404, which can be optionally included as part of neurostimulation programming circuitry 1406. The processor 1402 may be any single processor or group of processors that act cooperatively. The memory 1404 may be any type of memory, including volatile or non-volatile memory. The memory 1404 may include instructions, which when executed by the processor 1402, cause the processor 1402 to implement the features of the neurostimulation programming circuitry 1406. Thus, the electronic operations in the system 1400 may be performed by the processor 1402 or the circuitry 1406.

The processor 1402 or circuitry 1406 may directly or indirectly implement neurostimulation operations associated with the method 1200, including the use of further neurostimulation device programming based on processed data (operation 1212). The processor 1402 or circuitry 1406 may further provide data and commands to assist the processing and implementation of the programming using communication interface 1408. It will be understood that the processor 1402 or circuitry 1406 may also implement other aspects of the device data processing or device programming functionality described above with reference to FIGS. 6-12.

Figure 15:
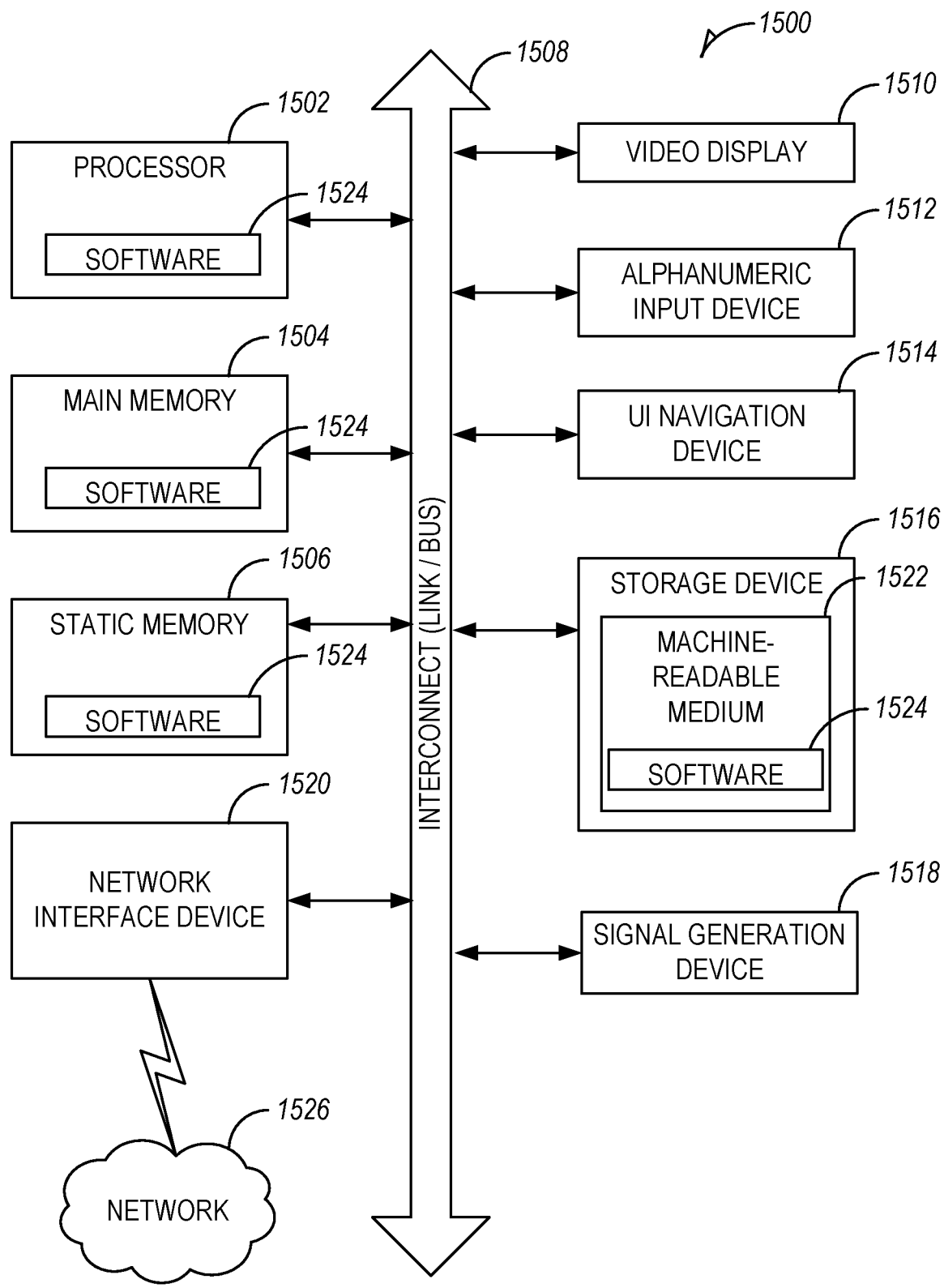
FIG. 15 is a block diagram illustrating a machine in the example form of a computer system, within which a set or sequence of instructions may be executed to cause the machine to perform any one of the methodologies discussed herein, according to an example embodiment.

FIG. 15 is a block diagram illustrating a machine in the example form of a computer system 1500, within which a set or sequence of instructions may be executed to cause the machine to perform any one of the methodologies discussed herein, according to an example embodiment. In alternative embodiments, the machine operates as a standalone device or may be connected (e.g., networked) to other machines. In a networked deployment, the machine may operate in the capacity of either a server or a client machine in server-client network environments, or it may act as a peer machine in peer-to-peer (or distributed) network environments. The machine may be a personal computer (PC), a tablet PC, a hybrid tablet, a personal digital assistant (PDA), a mobile telephone, an implantable pulse generator (IPG), an external remote control (RC), a User's Programmer (CP), or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Similarly, the term "processor-based system" shall be taken to include any set of one or more machines that are controlled by or operated by a processor (e.g., a computer) to individually or jointly execute instructions to perform any one or more of the methodologies discussed herein.

Example computer system 1500 includes at least one processor 1502 (e.g., a central processing unit (CPU), a graphics processing unit (GPU) or both, processor cores, compute nodes, etc.), a main memory 1504 and a static memory 1506, which communicate with each other via a link 1508 (e.g., bus). The computer system 1500 may further include a video display unit 1510, an alphanumeric input device 1512 (e.g., a keyboard), and a user interface (UI) navigation device 1514 (e.g., a mouse). In one embodiment, the video display unit 1510, input device 1512 and UI navigation device 1514 are incorporated into a touch screen display. The computer system 1500 may additionally include a storage device 1516 (e.g., a drive unit), a signal generation device 1518 (e.g., a speaker), a network interface device 1520, and one or more sensors (not shown), such as a global positioning system (GPS) sensor, compass, accelerometer, or other sensor. It will be understood that other forms of machines or apparatuses (such as PIG, RC, CP devices, and the like) that are capable of implementing the methodologies discussed in this disclosure may not incorporate or utilize every component depicted in FIG. 15 (such as a GPU, video display unit, keyboard, etc.).

The storage device 1516 includes a machine-readable medium 1522 on which is stored one or more sets of data structures and instructions 1524 (e.g., software) embodying or utilized by any one or more of the methodologies or functions described herein. The instructions 1524 may also reside, completely or at least partially, within the main memory 1504, static memory 1506, and/or within the processor 1502 during execution thereof by the computer system 1500, with the main memory 1504, static memory 1506, and the processor 1502 also constituting machine-readable media.

While the machine-readable medium 1522 is illustrated in an example embodiment to be a single medium, the term "machine-readable medium" may include a single medium or multiple media (e.g., a centralized or distributed database, and/or associated caches and servers) that store the one or more instructions 1524. The term "machine-readable medium" shall also be taken to include any tangible (e.g., non-transitory) medium that is capable of storing, encoding or carrying instructions for execution by the machine and that cause the machine to perform any one or more of the methodologies of the present disclosure or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including but not limited to, by way of example, semiconductor memory devices (e.g., electrically programmable read-only memory (EPROM), electrically erasable programmable read-only memory (EEPROM)) and flash memory devices; magnetic disks such as internal hard disks and removable disks; magneto-optical disks; and CD-ROM and DVD-ROM disks.

The instructions 1524 may further be transmitted or received over a communications network 1526 using a transmission medium via the network interface device 1520 utilizing any one of a number of well-known transfer protocols (e.g., HTTP). Examples of communication networks include a local area network (LAN), a wide area network (WAN), the Internet, mobile telephone networks, plain old telephone (POTS) networks, and wireless data networks (e.g., Wi-Fi, 3G, and 4G LTE/LTE-A or 5G networks). The term "transmission medium" shall be taken to include any intangible medium that is capable of storing, encoding, or carrying instructions for execution by the machine, and includes digital or analog communications signals or other intangible medium to facilitate communication of such software.

The above detailed description is intended to be illustrative, and not restrictive. The scope of the disclosure should, therefore, be determined with references to the appended claims, along with the full scope of equivalents to which such claims are entitled.

What is claimed is:

1. A device to process freeform data relating to neurostimulation treatment, the device comprising:
   at least one processor and at least one memory;
   input data processing circuitry, operable with the processor and the memory, the input data processing circuitry configured to:
      receive freeform input, the freeform input indicating one or more characteristics of a neurostimulation treatment of a human patient; and
      identify text from the freeform input;
   text processing circuitry, operable with the processor and the memory, the text processing circuitry configured to:
      validate the freeform input by identifying one or more words in the text and changing the text to produce a validated freeform input, based on natural language processing of the freeform input; and
      identify one or more attributes associated with a state of the human patient, based on one or more words from the validated freeform input; and
   patient state data processing circuitry, in operation with the at least one processor and the at least one memory, configured to:
      associate the one or more attributes with the validated freeform input; and
      output data for the validated freeform input and the one or more associated attributes.

2. The device of claim 1, wherein to validate the freeform input includes to:
   identify one or more words for exclusion in the freeform input, based on an exclusion word list; and
   remove the one or more words for exclusion from the freeform input, to produce the validated freeform input;
   wherein the exclusion word list is determined based on the natural language processing of the freeform input.

3. The device of claim 1, wherein to validate the freeform input includes to:
   identify one or more words for inclusion in the freeform input, based on an allowed word list; and
   select the one or more words for inclusion from the freeform input, to produce the validated freeform input;
   wherein the allowed word list is based on the natural language processing of the freeform input.

4. The device of claim 1, wherein to validate the freeform input includes to:
   anonymize the freeform input, to remove personally identifying information from the freeform input.

5. The device of claim 4, wherein to validate the freeform input further includes to:
   obtain user validation of the anonymized freeform input.

6. The device of claim 1, wherein the one or more attributes indicate a state of a medical condition or a state of the neurostimulation treatment for the human patient,
   wherein the one or more attributes are identified using natural language processing of the one or more words from the validated freeform input, and wherein to identify the one or more attributes includes to:
- identify the state of the medical condition from one or more of: medication data, sensor data, or neurostimulation device data; and
- identify the state of the neurostimulation treatment from one or more of: prior neurostimulation settings, current neurostimulation settings, or scheduled programmed neurostimulation settings.

7. The device of claim 1, wherein the state of the human patient relates to at least one physiological condition identified from the validated freeform input, and wherein the at least one physiological condition is associated with: pain measurements, pain states, sleep measurements, sleep states, movement, activity, mobility, physical function, cardiac function, autonomic function, medication, or emotional state, of the human patient.

8. The device of claim 1, wherein to associate the one or more attributes with the validated freeform input includes to:
- match use of at least one neurostimulation program to the state of the human patient, based on usage of the at least one neurostimulation program in a neurostimulation device implanted in the human patient.

9. The device of claim 1, wherein the freeform input originates from the human patient, a caregiver, or a medical professional associated with the human patient, and wherein the freeform input originates from a text input or an audio input converted to the identified text.

10. The device of claim 1, wherein to store the data includes causing the data to be stored in a remote database maintaining data for a plurality of human patients.

11. A method for processing freeform data relating to neurostimulation treatment, comprising:
- receiving freeform input, the freeform input indicating one or more characteristics of a neurostimulation treatment of a human patient;
- identifying text from the freeform input;
- validating the freeform input by identifying one or more words in the text and changing the text to produce a validated freeform input, based on natural language processing of the freeform input;
- identifying one or more attributes associated with a state of the human patient, based on one or more words from the validated freeform input;
- associating the one or more attributes with the validated freeform input; and
- storing data for the validated freeform input and the one or more associated attributes.

12. The method of claim 11, wherein validating the freeform input comprises:
- identifying one or more words for exclusion in the freeform input, based on an exclusion word list; and
- removing the one or more words for exclusion from the freeform input, to produce the validated freeform input;
- wherein the exclusion word list is determined based on the natural language processing of the freeform input.

13. The method of claim 11, wherein validating the freeform input comprises:
- identifying one or more words for inclusion in the freeform input, based on an allowed word list; and
- selecting the one or more words for inclusion from the freeform input, to produce the validated freeform input;
- wherein the allowed word list is based on the natural language processing of the freeform input.

14. The method of claim 11, wherein validating the freeform input comprises:
- anonymizing the freeform input, to remove personally identifying information from the freeform input.

15. The method of claim 14, wherein validating the freeform input comprises:
- obtaining user validation of the anonymized freeform input.

16. The method of claim 11, wherein the one or more attributes indicate a state of a medical condition or a state of the neurostimulation treatment for the human patient,
- wherein the one or more attributes are identified using natural language processing of the one or more words from the validated freeform input, and
- wherein identifying the one or more attributes further comprises:
  - identifying the state of the medical condition from one or more of: medication data, sensor data, or neurostimulation device data; and
  - identifying the state of the neurostimulation treatment from one or more of: prior neurostimulation settings, current neurostimulation settings, or scheduled programmed neurostimulation settings.

17. The method of claim 11, wherein the state of the human patient relates to at least one physiological condition identified from the validated freeform input, and wherein the at least one physiological condition is associated with: pain measurements, pain states, sleep measurements, sleep states, movement, activity, mobility, physical function, cardiac function, autonomic function, medication, or emotional state, of the human patient.

18. The method of claim 11, wherein associating the one or more attributes with the validated freeform input comprises:
- matching use of at least one neurostimulation program to the state of the human patient, based on usage of the at least one neurostimulation program in a neurostimulation device implanted in the human patient.

19. The method of claim 11, wherein the freeform input originates from the human patient, caregiver, or a medical professional associated with the human patient, and wherein the freeform input originates from a text input or an audio input converted to the identified text.

20. The method of claim 11, wherein to store the data comprises causing the data to be stored in a remote database maintaining data for a plurality of human patients.

* * * * *